US012778798B2

(12) United States Patent
Basilice et al.

(10) Patent No.: US 12,778,798 B2
(45) Date of Patent: Nov. 3, 2026

(54) ADAPTABLE PRECISION OCULAR FLUID MEDICATION DISPENSER

(71) Applicant: I IDEAS LLC, St. James, NY (US)

(72) Inventors: Vincent Prescott Basilice, St. James, NY (US); Matthew James Ibarra, Cerritos, CA (US); Benjamin Reyes Dadacay, Norwalk, CA (US); Dahna Marie Basilice, St. James, NY (US)

(73) Assignee: I IDEAS LLC, Greenport, NY (US)

( * ) Notice: Subject to any disclaimer, the term of this patent is extended or adjusted under 35 U.S.C. 154(b) by 0 days.

(21) Appl. No.: 18/921,142

(22) Filed: Oct. 21, 2024

(65) Prior Publication Data

US 2025/0041112 A1 Feb. 6, 2025

Related U.S. Application Data

(63) Continuation of application No. PCT/US2023/020230, filed on Apr. 27, 2023.

(60) Provisional application No. 63/336,948, filed on Apr. 29, 2022.

(51) Int. Cl.
*A61F 9/00* (2006.01)

(52) U.S. Cl.
CPC .................................. *A61F 9/0026* (2013.01)

(58) Field of Classification Search
CPC ..... A61F 9/0026; A61F 9/0008; A61H 35/02; A61M 35/003; A61M 2210/0612; A61M 11/006; A61M 11/008; B05B 11/00; B05B 12/002; G16H 20/13
See application file for complete search history.

(56) References Cited

U.S. PATENT DOCUMENTS

| | | | | | |
|---|---|---|---|---|---|
| 3,439,674 | A | * | 4/1969 | Lelicoff ................ | A61F 9/0008 D24/115 |
| 4,085,750 | A | * | 4/1978 | Bosshold .............. | A61F 9/0026 604/302 |
| 4,543,096 | A | * | 9/1985 | Keene ................... | A61F 9/0026 604/300 |
| 4,792,334 | A | * | 12/1988 | Py ......................... | A61F 9/0026 604/301 |
| 4,968,310 | A | * | 11/1990 | Menchel ............... | A61F 9/0008 222/206 |
| 5,267,986 | A | * | 12/1993 | Py ......................... | A61F 9/0008 222/336 |

(Continued)

OTHER PUBLICATIONS

International Search Report for counterpart PCT/US23/20230, filed Apr. 27, 2023 (6 pages).

*Primary Examiner* — Jessica Arble
*Assistant Examiner* — Arjuna P Chatrathi
(74) *Attorney, Agent, or Firm* — RowanTree Law Group, PLLC; Joseph W. Schmidt

(57) ABSTRACT

Various embodiments of an adaptable precision fluid medication dispenser system are disclosed. The adaptable precision fluid medication dispenser system can be configured to engage with a bottle and can include a nozzle, a fluid chamber, a collared cap, and an arm configured to engage with a lower eyelid area of a user. The arm can also be configured to deform the nozzle, the fluid chamber, or the bottle, causing fluid medication to be dispensed through the nozzle. Optionally, the adaptable precision fluid medication dispenser system can include a cover configured to act as a stand and engage with the nozzle and the arm.

30 Claims, 19 Drawing Sheets

(56) References Cited

U.S. PATENT DOCUMENTS

| | | | | | |
|---|---|---|---|---|---|
| 5,366,448 | A * | 11/1994 | Basilice | A61F 9/0026 604/300 |
| 5,387,202 | A | 2/1995 | Baron | |
| 5,578,020 | A * | 11/1996 | Mosley | A61F 9/0026 604/300 |
| 6,090,086 | A * | 7/2000 | Bolden | A61F 9/0026 604/300 |
| 6,423,040 | B1 * | 7/2002 | Benktzon | A61F 9/0008 604/300 |
| 7,435,241 | B1 * | 10/2008 | Dascanio | A61F 9/0008 604/300 |
| 2005/0107755 | A1 * | 5/2005 | Berger | A61F 9/0026 604/295 |
| 2009/0137972 | A1 * | 5/2009 | Katayama | B05B 11/1094 222/490 |
| 2009/0259204 | A1 * | 10/2009 | Galdeti | A61F 9/0026 222/173 |
| 2010/0022971 | A1 | 1/2010 | Marx | |
| 2012/0310184 | A1 * | 12/2012 | Pedersen | A61H 35/02 604/296 |

* cited by examiner

SECTION A-A

ADAPTABLE PRECISION OCULAR FLUID MEDICATION DISPENSER

CROSS-REFERENCE TO RELATED APPLICATION

This application is a continuation of PCT/US/2023/020230, filed Apr. 27, 2023, entitled "ADAPTABLE PRECISION OCULAR FLUID MEDICATION DISPENSER," which claims priority under 35 U.S.C. § 119(a) to U.S. Provisional application serial number No. 63/336,948, filed on Apr. 29, 2022 and entitled "ADAPTABLE PRECISION OCULAR FLUID MEDICATION DISPENSER," the disclosures of each being incorporated herein by their entireties.

BACKGROUND

Medications formulated for administration to the eye of a patient or subject are often dispensed in small volumes, making accurate dispensing of appropriate volumes of medication important. Additionally, the medications and formulations may be costly, therefore it is beneficial to reduce waste and avoid incorrect dispensing, both in terms of location accuracy and accurate volume being dispensed. Lastly, many seniors have difficulty with drop instillation secondary to arthritic conditions. They cannot squeeze the bottles to deliver the necessary medication.

The present invention relates generally to improvements for facilitating the dispensing of eye drops, the improvements more particularly obviating such prior art shortcomings, such as requiring a tilted-back head position, preventing inadvertent blinking and other occurrences during administration of the eye drops which are counterproductive to achieving the purposes intended.

Some commercially available squeeze bottle or equivalent eye drop dispensers may use positioning devices to direct dispensed eye drops onto the eye surface. However, currently known and available supports and dispensers have shortcomings. For example, such shortcomings include requiring special head positions and other special procedures or techniques that, at best, make self-application difficult and, more often, prevent the user from achieving proper eye treatment using eye drops. At least some prior art dispensers can even contribute to the spreading of an eye infection, such as with a contaminated dispenser.

The present invention can provide a safe and effective eye drop dispensing method and components, thereby overcoming the shortcomings of the prior art. Using the present invention, eye drops are more safely and efficiently administered, as well as reduce solution waste. This is of particular importance with certain medicinal eye solution drops, which are particularly expensive. Further, the present invention dispenses eye drops with the recipient's or patient's head in a natural position and otherwise with such ease that safe and correct self-application is possible. As such, the present invention may be used even by the elderly and by patients with poor eyesight, crippling arthritis, and/or other interfering handicaps.

Described and illustrated herein are implementations of an adaptable precision fluid dispenser, configured for use in dispensing medication formulations into the eye of a subject.

SUMMARY

Aspects of the current subject matter relate to various embodiments of an adaptable precision fluid dispenser system.

In one aspect, the adaptable precision fluid may include a nozzle assembly adaptable to a fluid container, the nozzle assembly including a nozzle, a compressible fluid chamber, and an arm. The nozzle may have a hollow cylindrical portion extending between a proximal end of the nozzle and a distal end of the nozzle. The compressible fluid chamber may be in fluid communication with the hollow cylindrical portion such that compression of the compressible fluid chamber may cause a volume of fluid to be dispensed from the nozzle. The arm may extend at an angle relative to the nozzle for assisting with dispensing the volume of fluid in an eye of a user.

In some variations, one or more of the following features can optionally be included in any feasible combination. For example, at least a part of the arm may be formed of a flexible material thereby allowing at least the part of the arm to bend and the arm to pivot relative to the nozzle. The arm may include a distal tip that is formed to engage skin adjacent the eye. The distal tip may include one or more of a hollow circular cylinder, a hollow ovular cylinder, and a rounded protrusion. The distal tip may include a smooth surface. The distal tip may include a surface texture. The surface texture may include one or more grooves and/or one or more protrusions. The distal tip may frictionally engage the lower eyelid thereby allowing the arm to move the lower eyelid away from the eye. The arm may extend relative to the nozzle such that positioning the distal tip in contact with a lower eyelid area of a user may position the distal end of the nozzle adjacent the eye for ensuring the volume of fluid is dispensed within a desired eye area. The arm may be deformable to allow the arm to pivot relative to the nozzle and/or the compressible fluid chamber thereby deforming the nozzle and/or the compressible fluid chamber and causing the volume of fluid to be dispensed from the nozzle. The arm may include a protrusion that may engage with one or more of the nozzle, the compressible fluid chamber, and the fluid container coupled to the nozzle assembly. The engaging may include deforming and/or compressing one or more of the nozzle, the compressible fluid chamber, and the fluid container. The adaptable precision fluid dispenser system may include a collared cap that releasably secures the nozzle assembly to the fluid container. The nozzle assembly may include a nozzle collar that releasably secures the nozzle assembly to the fluid container. The arm and the nozzle collar may be made of a first material, and the nozzle and the fluid chamber may be made of a second material, wherein the first material and the second material are different. The first material and the second material may have one or more of a different flexibility and a different stiffness. The nozzle assembly may include a backbone made of a rigid material, and the rigid material may be more rigid compared to a flexible material forming at least a part of one or more of the nozzle, the compressible fluid chamber, and the arm. The backbone may be engaged with at least a portion of the arm. The backbone may include one or more of a notch and a curved portion. The hollow cylindrical portion of the nozzle may taper toward the distal end of the nozzle. The adaptable precision fluid dispenser system may include a cover that may engage with the nozzle assembly. The cover may occlude the distal end of the nozzle. The cover may include a flat portion and may act as a stand. The compressible fluid chamber may be dome-shaped, hemispherical, or partially spherical. The volume may be approximately 5 microliters (uL) to approximately 15 uL.

In another interrelated aspect of the current subject matter, a method of using an adaptable precision fluid dispenser system may include coupling a nozzle assembly of the adaptable precision fluid dispenser system to a fluid container, and the nozzle assembly may include a nozzle, a compressible fluid chamber, and an arm. The nozzle may have a hollow cylindrical portion extending between a proximal end of the nozzle and a distal end of the nozzle. The compressible fluid chamber may be in fluid communication with the hollow cylindrical portion such that compression of the compressible fluid chamber may cause a volume of fluid to be dispensed from the nozzle. The arm may extend at an angle relative to the nozzle for assisting with dispensing the volume of fluid in an eye of a user.

In some embodiments, at least a part of the arm may be formed of a flexible material thereby allowing at least the part of the arm to bend and the arm to pivot relative to the nozzle. The arm may include a distal tip that is formed to engage skin adjacent the eye. The distal tip may include one or more of a hollow circular cylinder, a hollow ovular cylinder, and a rounded protrusion. The distal tip may include a smooth surface. The distal tip may include a surface texture. The surface texture may include one or more grooves and/or one or more protrusions. The distal tip may frictionally engage the lower eyelid thereby allowing the arm to move the lower eyelid away from the eye. The arm may extend relative to the nozzle such that positioning the distal tip in contact with a lower eyelid area of a user may position the distal end of the nozzle adjacent the eye for ensuring the volume of fluid is dispensed within a desired eye area. The arm may be deformable to allow the arm to pivot relative to the nozzle and/or the compressible fluid chamber thereby deforming the nozzle and/or the compressible fluid chamber and causing the volume of fluid to be dispensed from the nozzle. The arm may include a protrusion that may engage with one or more of the nozzle, the compressible fluid chamber, and the fluid container coupled to the nozzle assembly. The engaging may include deforming and/or compressing one or more of the nozzle, the compressible fluid chamber, and the fluid container. The adaptable precision fluid dispenser system may include a collared cap that releasably secures the nozzle assembly to the fluid container. The nozzle assembly may include a nozzle collar that releasably secures the nozzle assembly to the fluid container. The arm and the nozzle collar may be made of a first material, and the nozzle and the fluid chamber may be made of a second material, wherein the first material and the second material are different. The first material and the second material may have one or more of a different flexibility and a different stiffness. The nozzle assembly may include a backbone made of a rigid material, and the rigid material may be more rigid compared to a flexible material forming at least a part of one or more of the nozzle, the compressible fluid chamber, and the arm. The backbone may be engaged with at least a portion of the arm. The backbone may include one or more of a notch and a curved portion. The hollow cylindrical portion of the nozzle may taper toward the distal end of the nozzle. The adaptable precision fluid dispenser system may include a cover that may engage with the nozzle assembly. The cover may occlude the distal end of the nozzle. The cover may include a flat portion and may act as a stand. The compressible fluid chamber may be dome-shaped, hemispherical, or partially spherical. The volume may be approximately 5 microliters (uL) to approximately 15 uL.

DETAILED DESCRIPTION

The present disclosure describes various embodiments of an adaptable precision fluid medication dispenser that can be used in the dispensing of eye medications, treatments or other solutions. The adaptable precision fluid medication dispenser allows for greater control over the volume of fluid dispensed, and the location of the fluid being dispensed. The adaptable precision fluid medication dispenser allows for improved dosing and patient comfort, as well as easy application, and use of the full volume of fluid in a bottle. The adaptable precision fluid medication dispenser can optionally include a cover and/or stand, configured to hold a bottle of fluid while also protecting the nozzle of the adaptable precision fluid medication dispenser from unhygienic situations. In general, the adaptable precision fluid medication dispenser includes an adapter configured to attach the dispenser to a bottle of fluid, a nozzle configured to dispense a small volume of fluid to the eye of a patient, and an arm or actuating mechanism configured to engage with the lower eyelid area of the patient such as to direct the location of dispensing, and can be further configured to deform one or both of the nozzle or the bottle sufficiently to disrupt the surface tension of the fluid in the nozzle and dispense the small volume of fluid to the eye of the patient. Various embodiments of the adaptable precision fluid medication dispenser system are described in detail below.

Figure 1D:
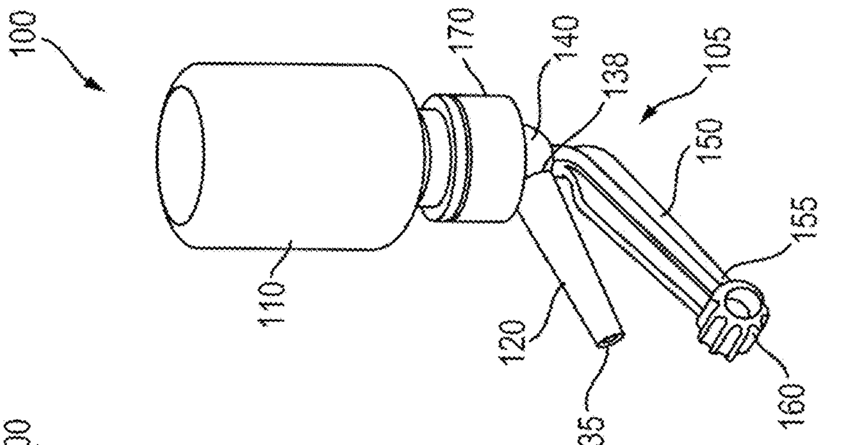
FIG. 1D is a top perspective view of the adaptable precision fluid medication dispenser of FIG. 1A.
Figure 1C:
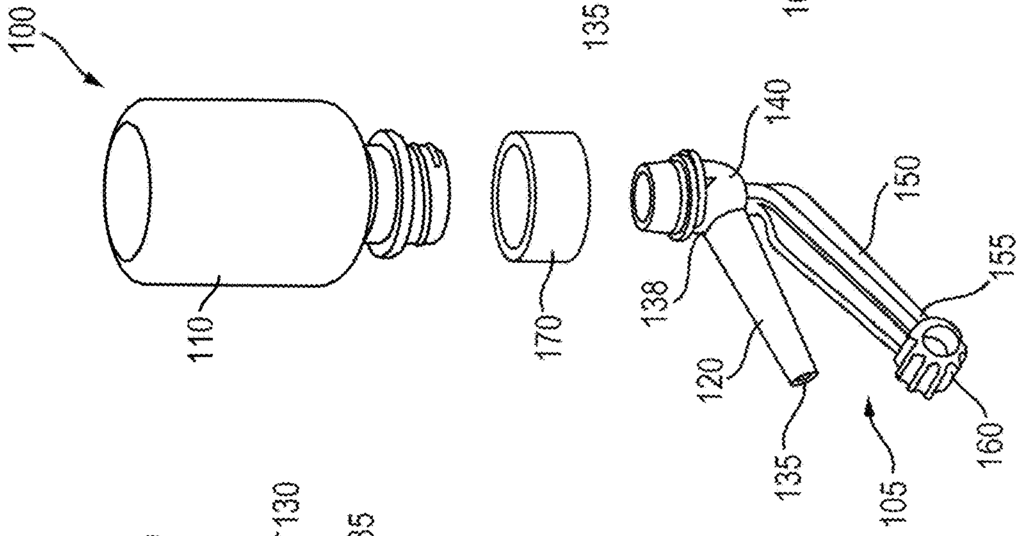
FIG. 1C is an exploded view of the adaptable precision fluid medication dispenser of FIG. 1A.
Figure 1B:
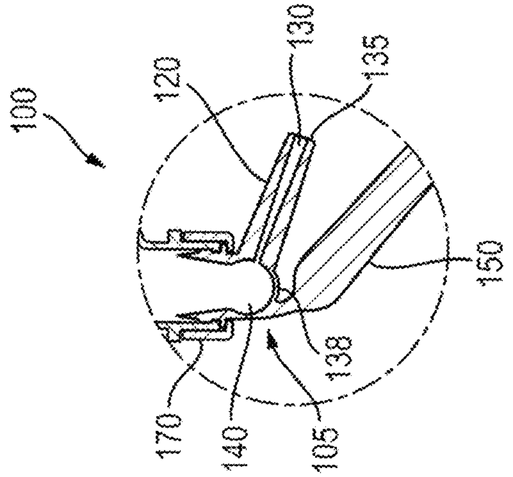
FIG. 1B is a cross sectional view of a nozzle of the adaptable precision fluid medication dispenser of FIG. 1A.
Figure 1A:
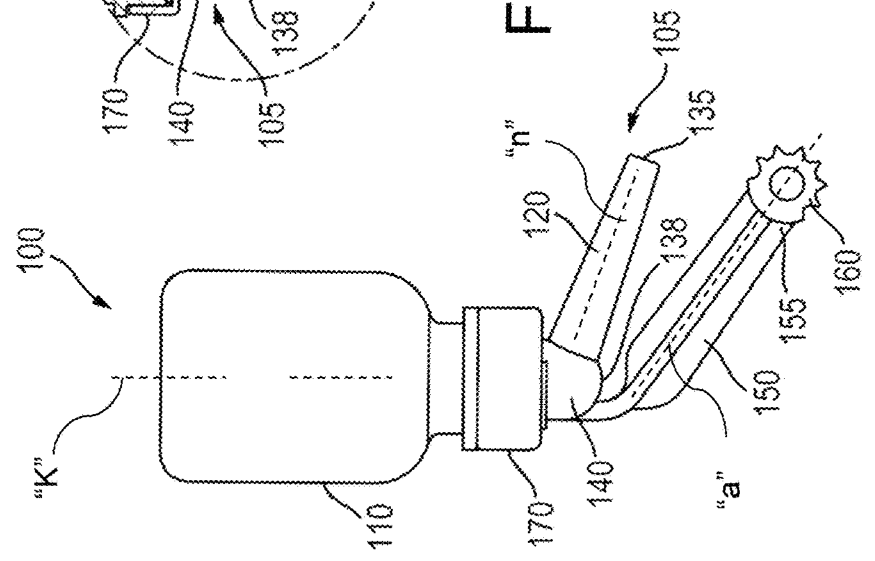
FIG. 1A is a side perspective view of a first embodiment of an adaptable precision fluid medication dispenser.

FIGS. 1A-1G illustrate a first embodiment of an adaptable precision fluid medication dispenser system 100, which can include a nozzle assembly 105 and, optionally, a container or bottle 110. FIG. 1A shows the nozzle assembly 105 of the adaptable precision fluid medication dispenser system 100 attached to a standard eyedropper bottle 110. The nozzle assembly 105 may be permanently or removably attached to the container or bottle 110. For example, the nozzle assembly 105 of the adaptable precision fluid medication dispenser system 100 may be configured to dispense fluid in consistent doses of approximately 5 microliters (uL) to approximately 15 uL, such as approximately 10 uL. As shown in FIG. 1B, the nozzle assembly 105 includes a nozzle 120 that can include a hollow cylindrical portion 130 with a cylindrical tapering structure that narrows from a proximal end 138 toward a distal end 135. The distal end 135 may be rounded. As shown in FIG. 1C, the nozzle assembly 105 can further be configured to fit, for example via press-fit, into a standard bottle orifice of a common eyedropper bottle 110. To accurately apply medication and reduce waste, the bottle 110 is oriented upside-down when attached to the nozzle assembly 105, forming adaptable precision fluid medication dispenser system 100. The nozzle assembly 105 can further include a dome structure configured to function as a fluid chamber 140 that contains at least a portion of a volume of fluid, for example liquid eye mediation. The fluid chamber 140 can fluidly communicate with the nozzle 120 and may be dome-shaped, hemispherical, or partially spherical. The proximal end 138 of the nozzle 120 may be attached to the fluid chamber 140. The nozzle 120 may comprise a flexible or deformable material, such as a plastic, polymer, or the like, and the volume of fluid contained within the hollow cylindrical portion 130 of the nozzle 120 may be held in place by surface tension between the fluid and the material of the nozzle 120. The nozzle 120 may be further configured such that deforming the hollow cylindrical portion 130, such as by pressing or squeezing the nozzle 120, causes sufficient disruption in surface tension to dispense a dose volume of fluid. The flexible or deformable material of the nozzle 120 may allow the hollow cylindrical portion 130 to reform after deformation to once again retain a volume of fluid via surface tension, after dispensing the dose volume of fluid. Additionally and/or alternatively, the bottle 110 may be deformed such that additional pressure is placed on the fluid chamber 140, forcing a dose volume of fluid to be dispensed from the hollow cylindrical portion 130 of the nozzle 120. Additionally and/or alternatively, the fluid chamber 140 may be deformed such that a dose volume of fluid is dispensed from the hollow cylindrical portion 130 of the nozzle 120.

Figure 1G:
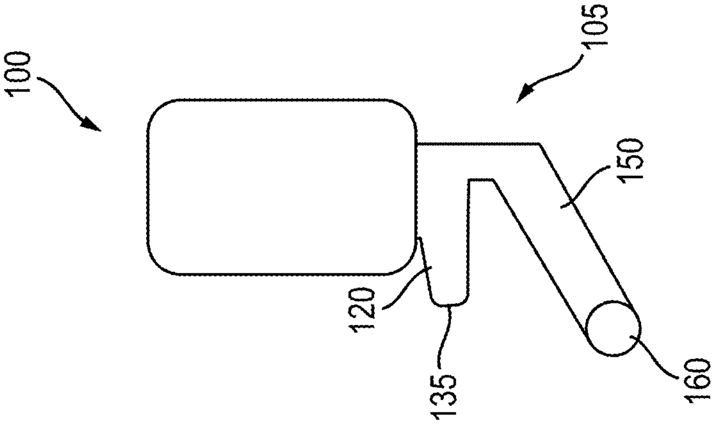
FIGS. 1E-1G illustrate side schematic views of the adaptable precision fluid medication dispenser showing different angling of the arm relative to the nozzle.
Figure 1F:
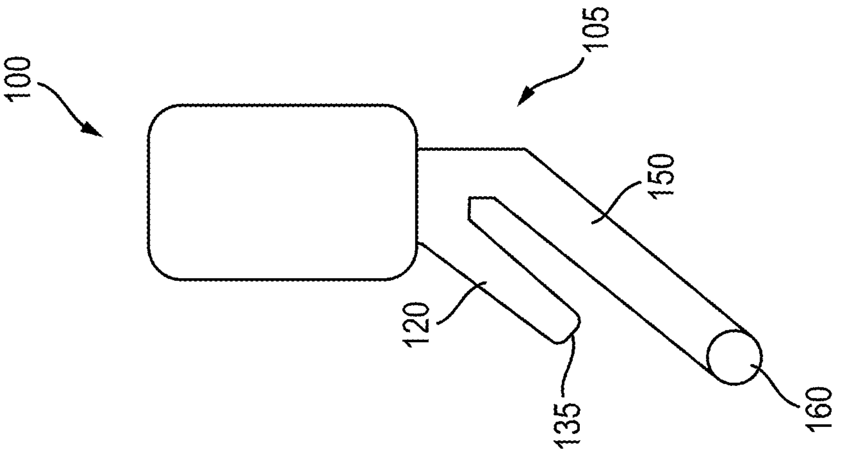
Figure 1E:
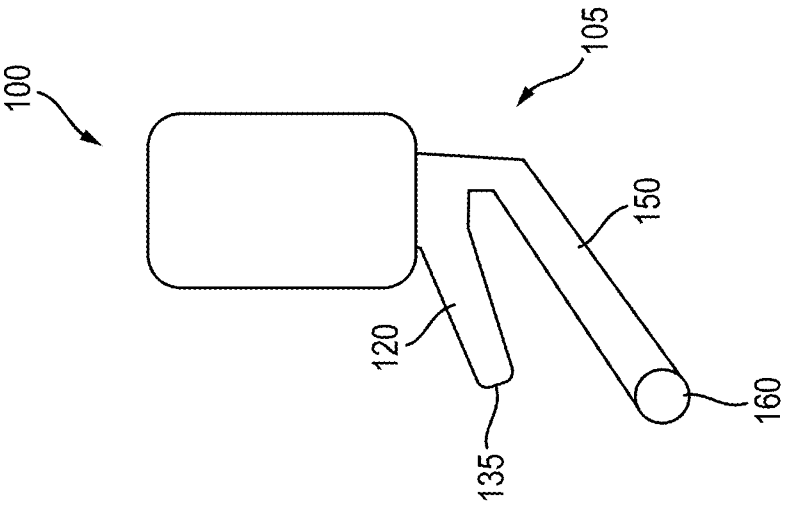
Figure 2D:
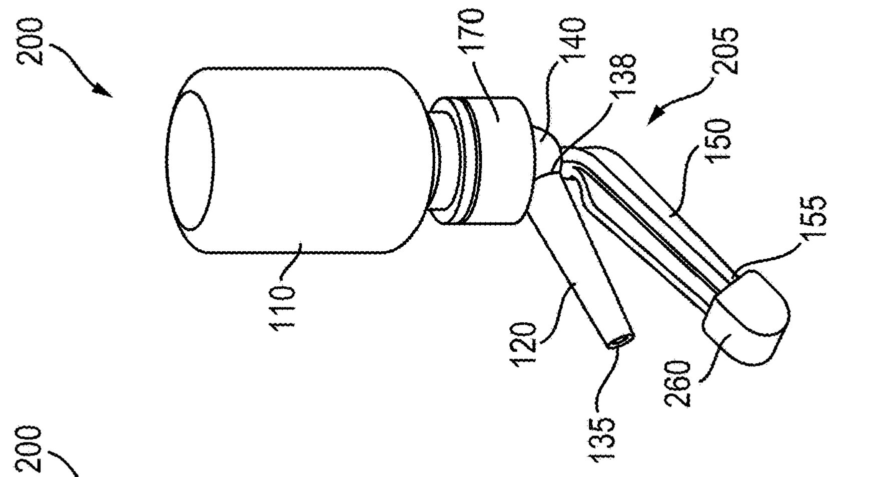
FIG. 2D is a top perspective view of the adaptable precision fluid medication dispenser of FIG. 2A.
Figure 2C:
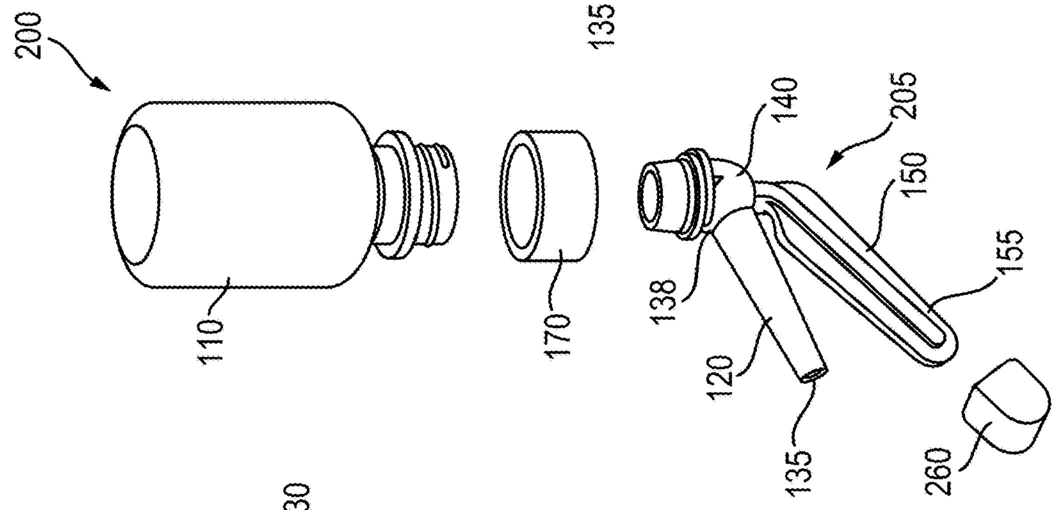
FIG. 2C is an exploded view of the adaptable precision fluid medication dispenser of FIG. 2A.
Figure 2B:
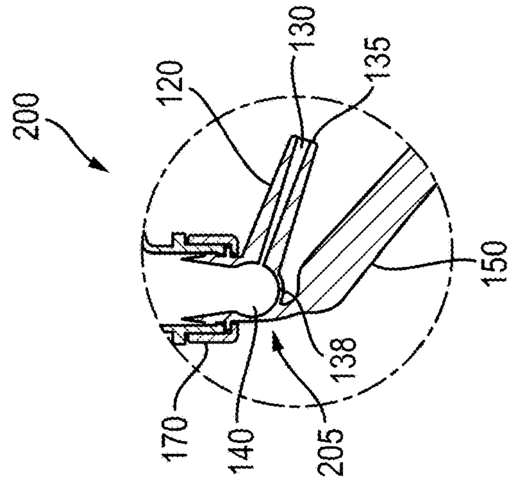
FIG. 2B is a cross sectional view of a nozzle of the adaptable precision fluid medication dispenser of FIG. 2A.
Figure 2A:
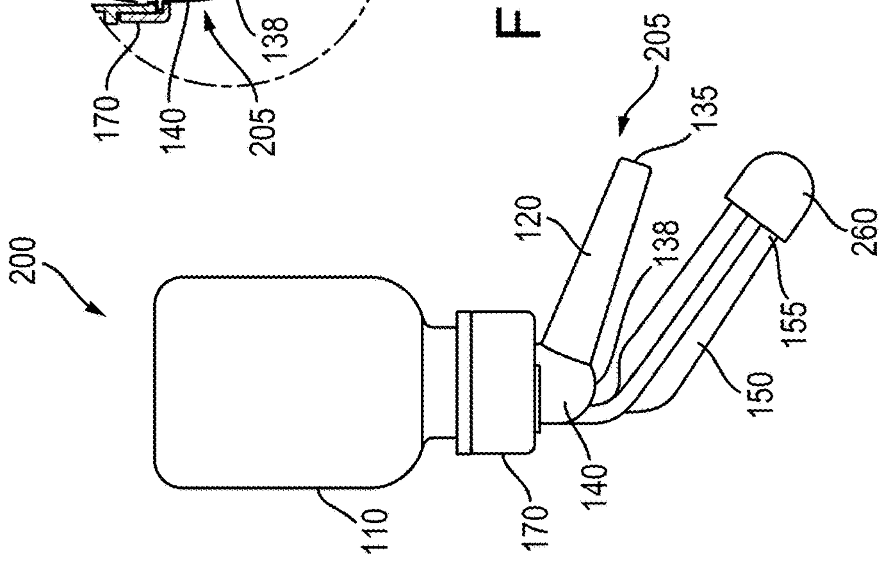
FIG. 2A is a side perspective view of a second embodiment of an adaptable precision fluid medication dispenser.
Figures 3A, 3B, 3C, 3D:
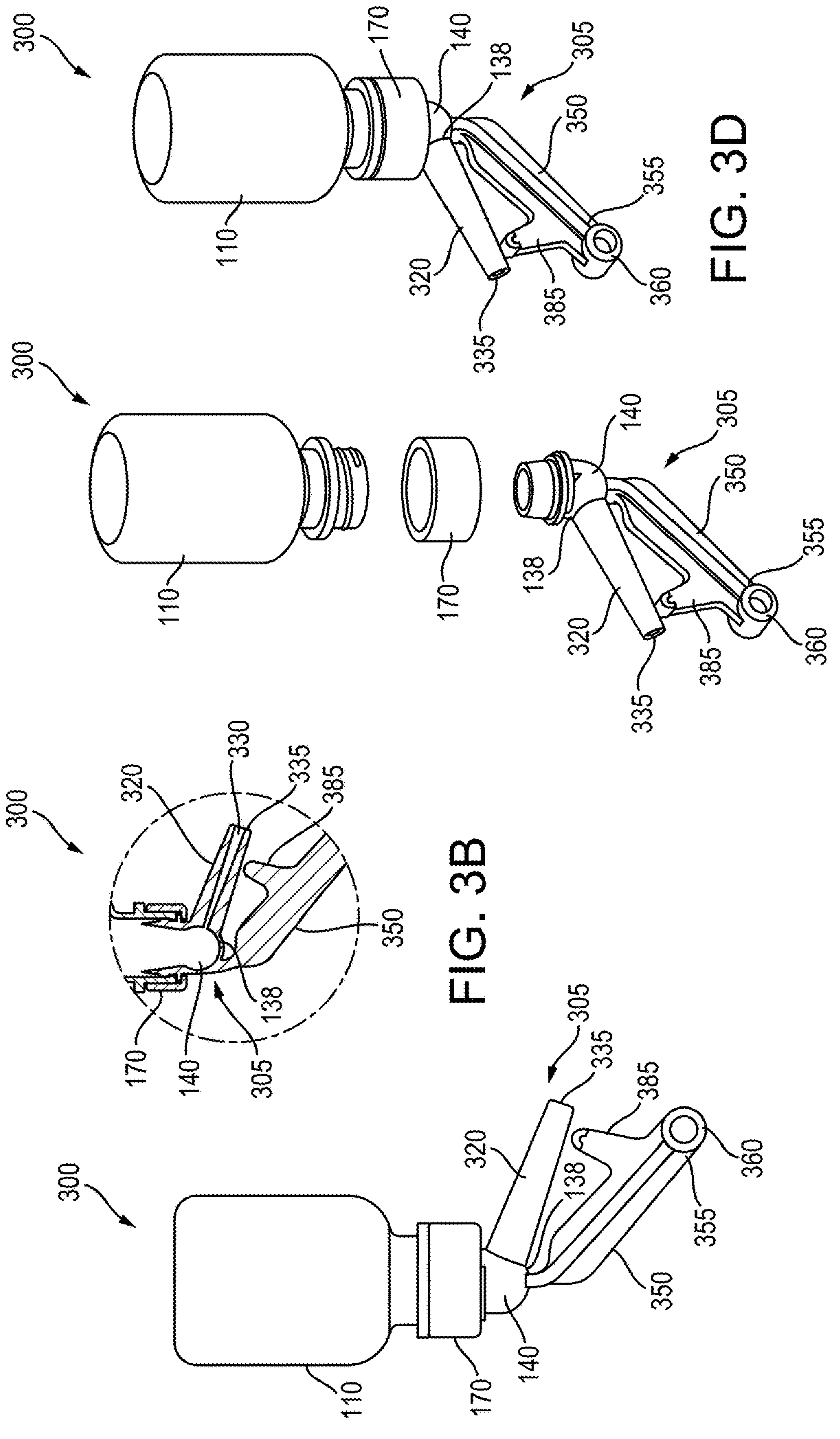
FIG. 3A is a side perspective view of a third embodiment of an adaptable precision fluid medication dispenser.
FIG. 3B is a cross sectional view of a nozzle of the adaptable precision fluid medication dispenser of FIG. 3A.
FIG. 3C is an exploded view of the adaptable precision fluid medication dispenser of FIG. 3A.
FIG. 3D is a top perspective view of the adaptable precision fluid medication dispenser of FIG. 3A.
Figure 4A:
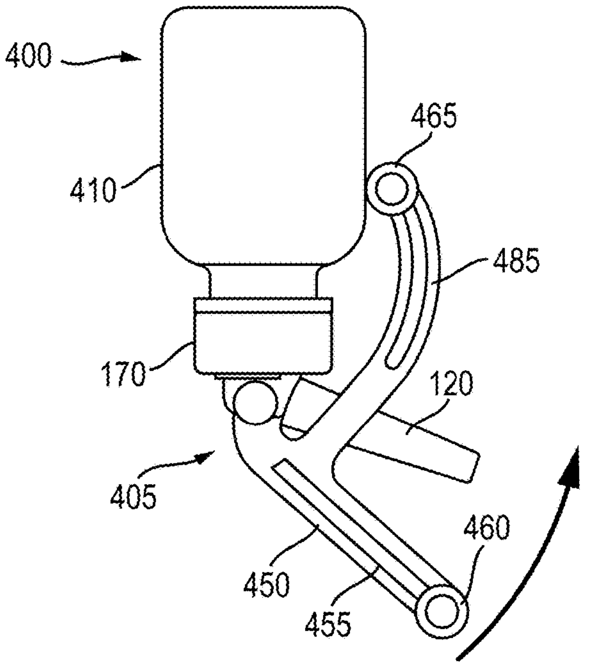
FIG. 4A is a side plan view of a fourth embodiment of an adaptable precision fluid medication dispenser in a disengaged position.
Figure 4B:
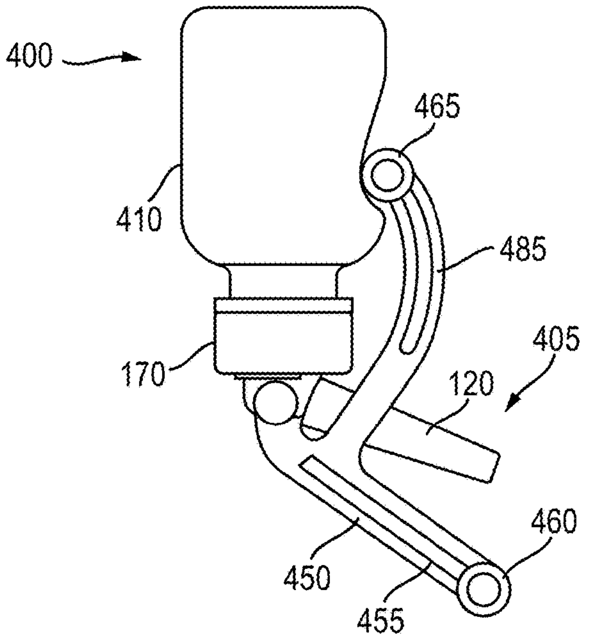
FIG. 4B is a side plan view of the adaptable precision fluid medication dispenser of FIG. 4A in an engaged position.
Figure 4C:
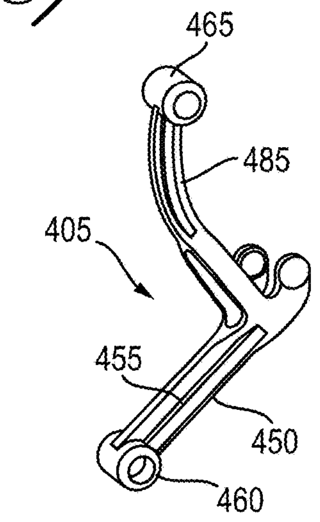
FIG. 4C is a top perspective view of the arm of the adaptable precision fluid medication dispenser of FIG. 4A.
Figure 4D:
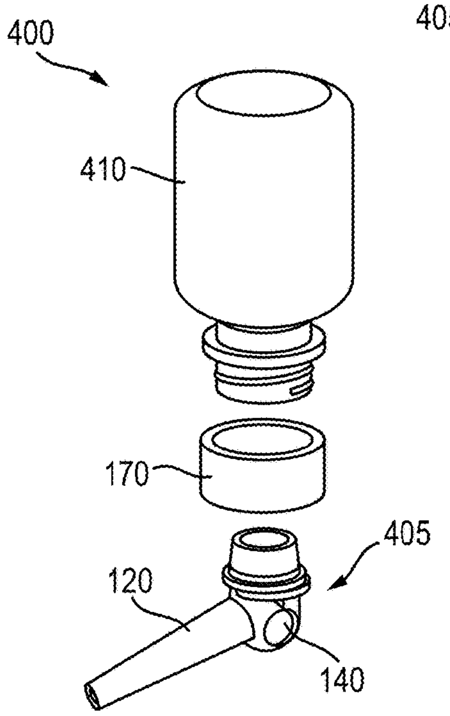
FIG. 4D is an exploded view of the adaptable precision fluid medication dispenser of FIG. 4A.
Figure 4E:
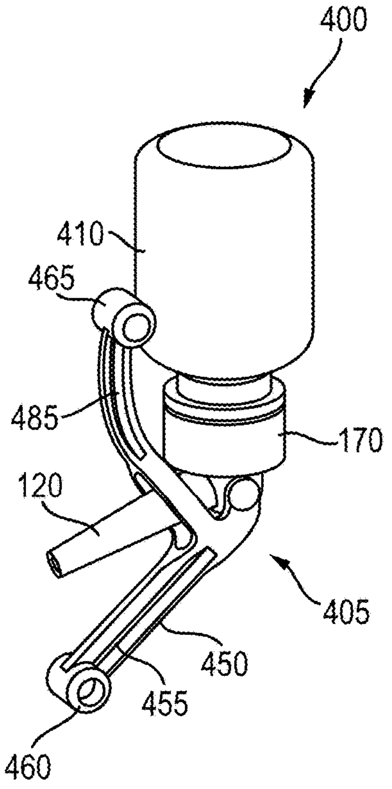
FIG. 4E is a top perspective view of the adaptable precision fluid medication dispenser of FIG. 4A.

The nozzle assembly 105 can further include an arm 150 extending from and/or adjacent to one or more of the proximal end 138 of the nozzle 120 and the fluid chamber 140. The arm 150 is generally arranged about or extends along an arm axis "a" and can extend outwardly away from the bottle 110 at an angle (e.g., relative to a longitudinal axis "k" of the bottle 110) such that a distal end 155 of the arm 150 is a longitudinal distance (y) and a horizontal distance (x) from the distal end 135 of the nozzle 120, as shown in schematic FIGS. 1E-1G. As shown in FIGS. 1E-1G, the arm 150 (e.g., the arm axis "a") can extend a variety of angles relative to the nozzle 120 while still positioning the distal end 155 of the arm 150 at an approximately same longitudinal distance (y) and same horizontal distance (x) relative to the distal end 135 of the nozzle 120.

For example the longitudinal distance (y) can be approximately 0.5 inch (in) to 1.0 in, and the horizontal distance (x) can be approximately 0.05 in to 0.3 in. In some embodiments, the nozzle 120 is generally arranged about or extends along a nozzle axis "n" and can extend at an angle relative to a horizontal axis (e.g., extending perpendicular to the longitudinal axis "k" of the bottle 110) within a range of approximately 15 degrees to 25 degrees (or about 65 degrees to about 75 degrees relative to the longitudinal axis "k"). In some embodiments, the arm 150 (e.g., the arm axis "a") can extend at an angle relative to the horizontal axis within a range of approximately 30 degrees to 50 degrees (or about 40 degrees to about 60 degrees relative to the longitudinal axis "k"). As shown in FIGS. 1E-1G, the distal end 155 of the arm 150 extends further away from the bottle 110 compared to the distal end 135 of the nozzle 120 in both the horizontal and longitudinal directions, as shown in FIGS. 1E-1G. The nozzle assembly 105 can have such a configuration to ensure safe and effective placement of the distal end 135 of the nozzle 120 relative to the eye (e.g., for dispensing medicament in the eye) when the distal end 155 of the arm 150 is positioned along the lower eyelid area of the patient or user in preparation for dispending medicament in the eye.

As shown in FIGS. 1A-1G, the distal end 155 of the arm 150 can extend in substantially the same direction as the nozzle 120. In some embodiments, the arm 150 may include a semi flexible/deformable section (e.g., a living hinge) near the proximal end of the arm 150 such that the arm 150 can slightly bend or pivot relative to the nozzle 120. Such relative pivoting can assist with safely and effectively dispending medicament from the bottle 110 to an eye area of a user, as will be described below.

The distal end 155 of the arm 150 may include a skin engagement feature 160, configured to engage the lower eyelid area of the patient and direct the location of the fluid being dispensed. For example, the skin engagement feature 160 may move the patients lower eyelid downward and provide a more suitable area for dispensing of the fluid. The skin engagement feature 160 may include grooves or protrusions to help engage the skin of the patient. When using the adaptable precision fluid medication dispenser system 100, the user will orient the nozzle 120 toward their eye and place the skin engagement feature 160 below the lower eyelid and with the distal end 135 of the nozzle 120 near the bottom of the eyeball but not in contact with the eyeball. The user may then pull or press on the bottle 110, applying force to the skin engagement feature sufficient to move the lower eyelid downward and create a desired eye area such as an opening below the eyelid, into which the fluid may be dispensed.

The nozzle assembly 105 may further include two or more horizontal ledges located on or adjacent to the fluid chamber 140, extending radially on opposite sides from the hollow cylindrical portion 130 and designed to rest on the edge of a standard squeeze bottle, each of the two or more horizontal ledges having a vertical wall stop.

Additionally, as shown in FIG. 1C, the adaptable precision fluid medication dispenser system 100 can optionally include a collared cap 170 to secure the nozzle assembly 105 in place by capturing the horizontal ledge of the nozzle assembly 105 and threading around the standard bottle 110 threads. The collared cap 170 can include a round cylindrical structure, open on the top and bottom faces, and inner threads configured to interface with a standard bottle 110, and two or more horizontal structures configured to interface with the ledges of the nozzle assembly 105 and capture the bottle 110.

As will be described in further detail below, the adaptable precision fluid medication dispenser system 100 may further include a cover configured to fit around at least a part of the adaptable precision fluid medication dispenser system 100, such as cover the nozzle 120 and arm 150. The cover can be configured to protect the adaptable precision fluid medication dispenser system 100 for cleanliness and sanitary purposes. The cover may further be configured to act as a stand, designed to stand on a flat surface and hold at least a part of the adaptable precision fluid medication dispenser system 100 while preventing spilling, leaking, tilting, or falling.

FIGS. 2A-2D illustrate a second embodiment of the adaptable precision fluid medication dispenser system 200 which includes features that are the same as or substantially similar to such features described above with respect to FIGS. 1A-1D, such that those features and their functions will not be repeated here for the sake of brevity. In some embodiments, such as that shown in FIGS. 2A-2D, nozzle assembly 205 includes a skin engagement feature 260 that can be rounded and/or removable and can have a smooth surface for engaging the skin of the patient.

FIGS. 3A-3D illustrate a third embodiment of the adaptable precision fluid medication dispenser system 300 which includes features that are the same as or substantially similar to such features described above with respect to FIGS. 1A-1D, such that those features and their functions will not be repeated here for the sake of brevity. In some embodiments, such as that shown in FIGS. 3A-3D, nozzle assembly 305 can include a nozzle 320, an arm 350, a skin engagement feature 360, and a fluid chamber 140. The arm 350 can include a protrusion 385 configured to engage with the nozzle 320 and deform the hollow cylindrical portion 330. Protrusion 385 can be located on or adjacent to distal end 355 of arm 350, and can engage with distal end 335 of nozzle 320. The skin engagement feature 360 can have a hollow cylindrical shape and can have a smooth surface for engaging the skin of the patient.

FIGS. 4A-4E illustrate a fourth embodiment of the adaptable precision fluid medication dispenser system 400 which includes features that are the same as or substantially similar to such features described above with respect to FIGS. 1A-1D, such that those features and their functions will not be repeated here for the sake of brevity. In some embodiments, such as that shown in FIGS. 4A-4E, nozzle assembly 405 can include a nozzle 120, a fluid chamber 140, and an arm 450. The arm 450 may include a secondary arm 485 configured to engage with the bottle 410 and deform the bottle 410 to dispense the fluid. The arm 450 can include a skin engagement feature 460 located on or adjacent to distal end 455 of the arm 450. The secondary arm 485 can include a bottle engagement feature 465 to engage with and deform the bottle 410. One or more of the skin engagement feature 460 and the bottle engagement feature 465 can have a hollow cylindrical shape with a smooth surface or a textured surface.

Figure 5C:
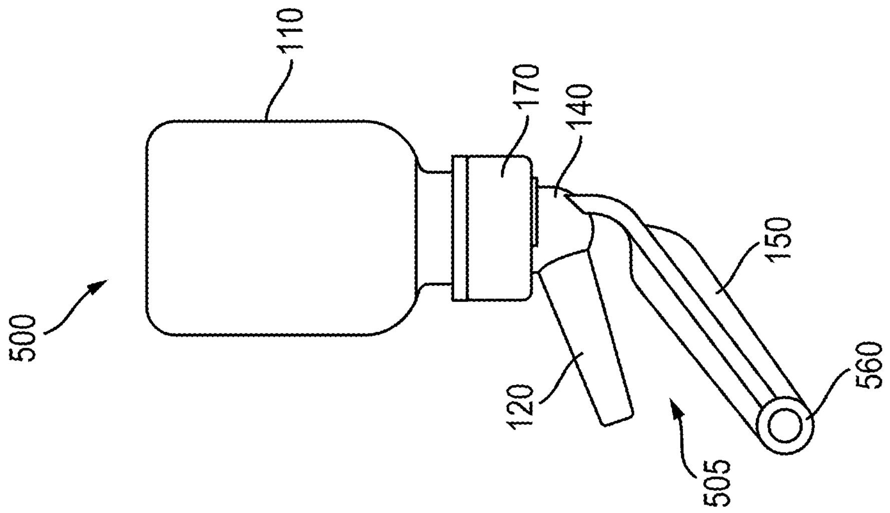
FIG. 5C is a side plan view of the adaptable precision fluid medication dispenser of FIG. 5A.
Figure 5B:
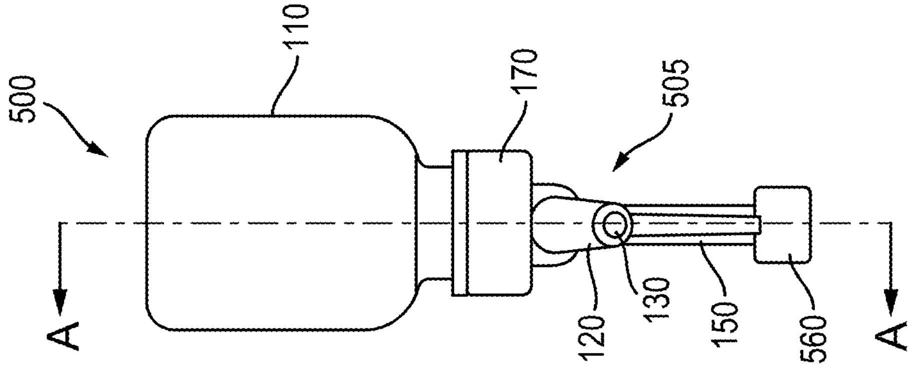
FIG. 5B is a front plan view of the adaptable precision fluid medication dispenser of FIG. 5A.
Figure 5A:
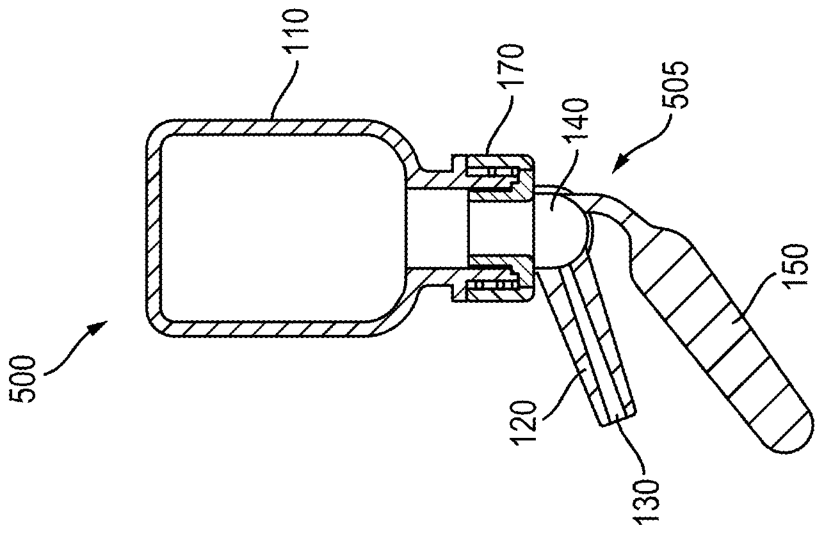
FIG. 5A is a side cross sectional view of a fifth embodiment of an adaptable precision fluid medication dispenser.

FIGS. 5A-5C illustrate a fifth embodiment of the adaptable precision fluid medication dispenser system 500 which includes features that are the same as or substantially similar to such features described above with respect to FIGS. 1A-1D, such that those features and their functions will not be repeated here for the sake of brevity. FIG. 5A shows a cross section of the adaptable precision fluid medication dispenser system 500 along the lines indicated in FIG. 5B. As shown in FIGS. 5B and 5C, nozzle assembly 505 can include a skin engagement feature 560 that is a hollow cylindrical shape and can have a smooth surface.

Figure 6E:
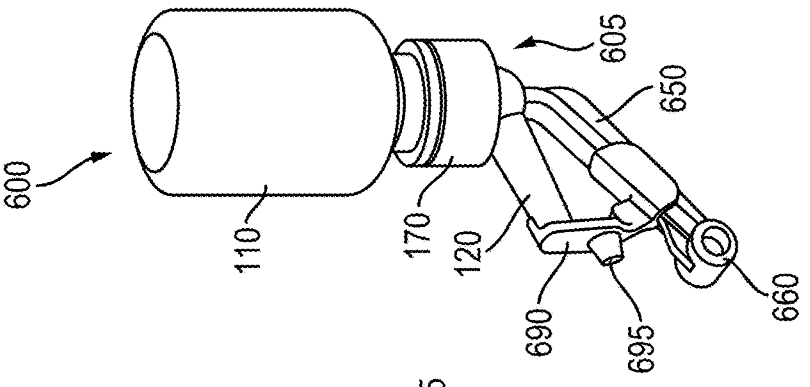
FIG. 6E is a top perspective view of the adaptable precision fluid medication dispenser and cover of FIG. 6A.
Figure 6D:
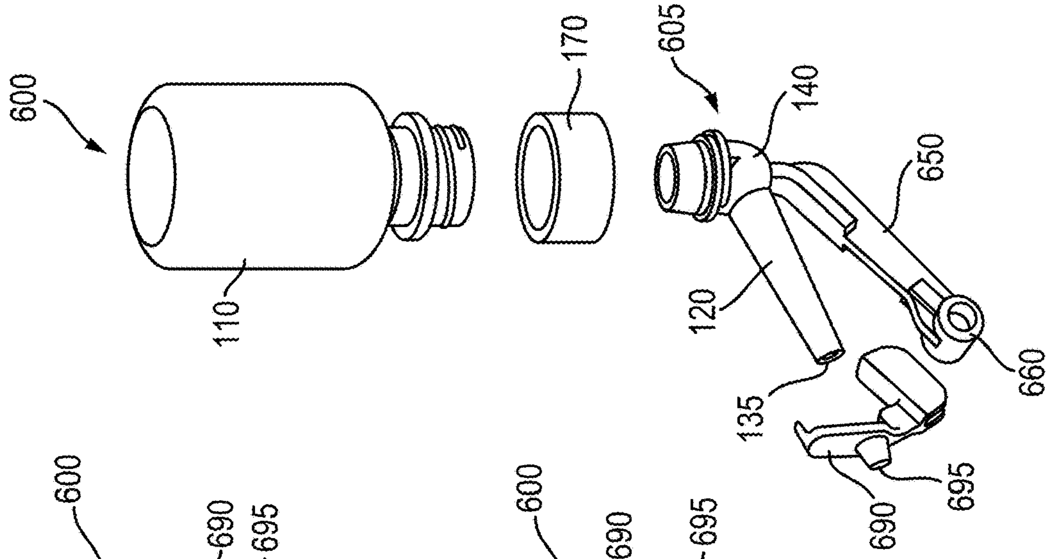
FIG. 6D is an exploded view of the adaptable precision fluid medication dispenser and cover of FIG. 6A.
Figure 6B:
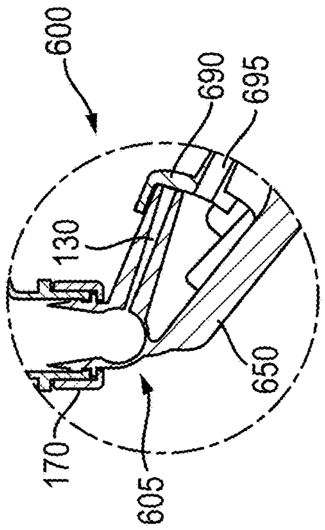
FIG. 6B is a side plan view of the nozzle of the adaptable precision fluid medication dispenser and cover of FIG. 6A in a disengaged position.
Figure 6C:
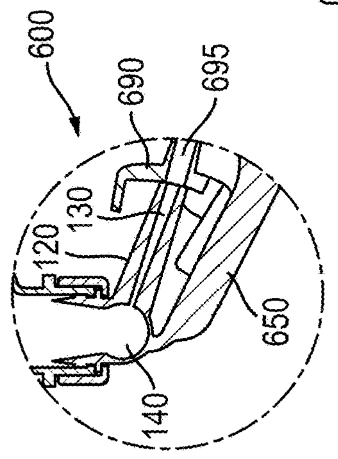
FIG. 6C is a side plan view of the nozzle of the adaptable precision fluid medication dispenser and cover of FIG. 6A in an engaged position.
Figure 6A:
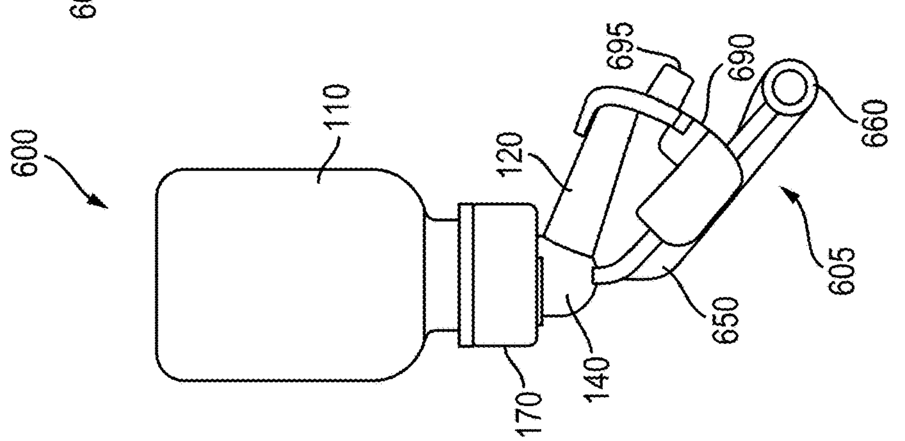
FIG. 6A is a side plan view of an sixth embodiment of an adaptable precision fluid medication dispenser and a first embodiment of a cover.

FIGS. 6A-6E illustrate a sixth embodiment of an adaptable precision fluid medication dispenser system 600, further including a first embodiment of a cover 690, which includes features that are the same as or substantially similar to such features described above with respect to FIGS. 1A-1D, such that those features and their functions will not be repeated here for the sake of brevity. As shown in FIGS. 6A-6E, the nozzle assembly 605 can include an arm 650, a skin engagement feature 660, a fluid chamber 140, and a nozzle 120. In some embodiments, such as that shown in FIGS. 6A-6E, the cover 690 may contain the distal end 135 of the nozzle 120, and may engage with the arm 650. As shown in FIG. 6B, the cover 690 may occlude the distal end 135 of the nozzle 120 when in a disengaged position. As shown in FIG. 6C, the cover 690 may include an opening 695 which aligns with the distal end 135 of the nozzle 120 when in an engaged position, to dispense fluid through the hollow cylindrical portion 130 and the opening 695 of the cover 690.

Figure 7C:
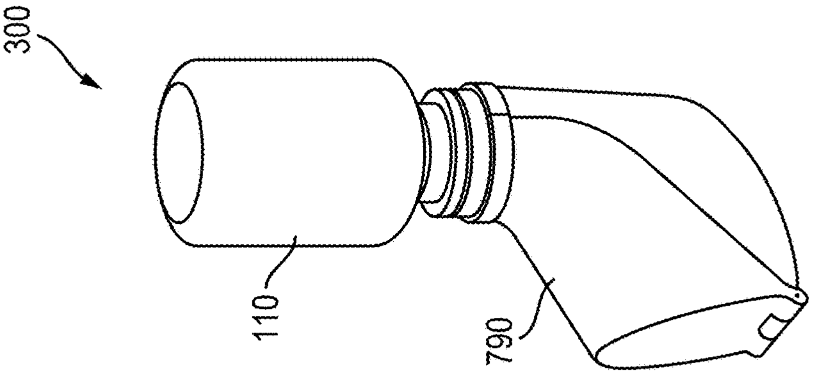
FIG. 7C is a top perspective view of the adaptable precision fluid medication dispenser and cover with stand of FIG. 7A in a closed position.
Figure 7B:
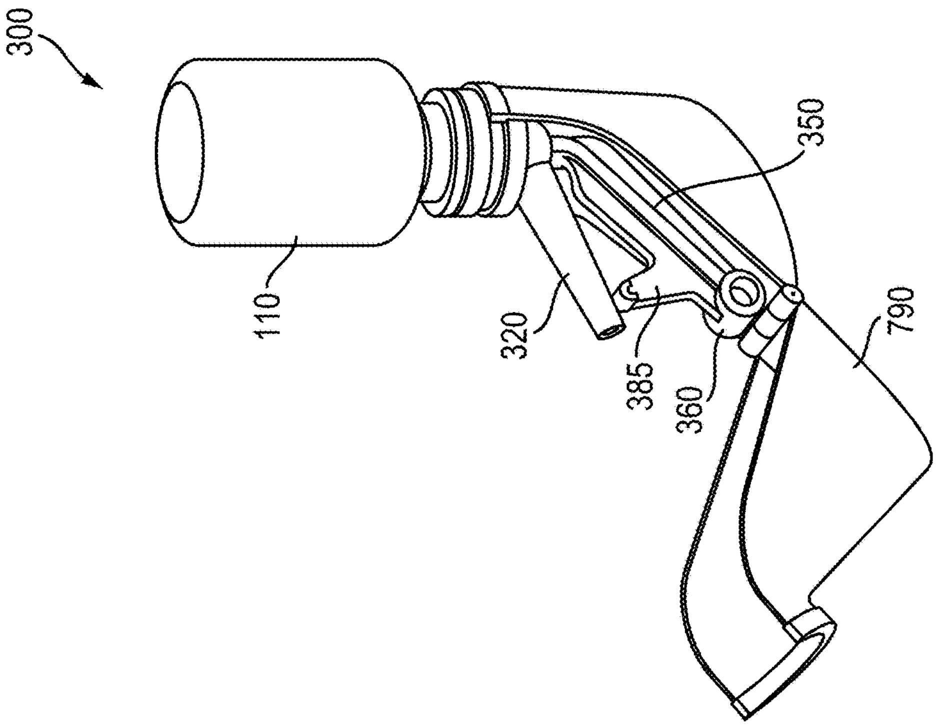
FIG. 7B is a top perspective view of the adaptable precision fluid medication dispenser and cover with stand of FIG. 7A in an open position.
Figure 7A:
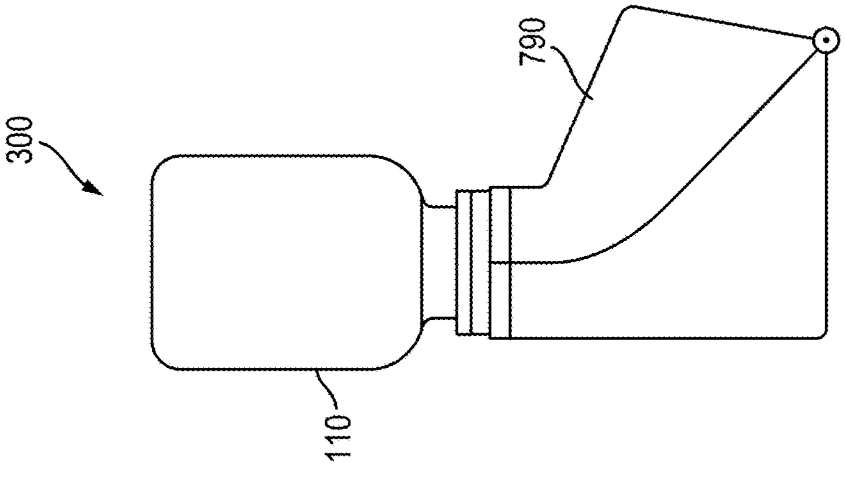
FIG. 7A is a side plan view of the adaptable precision fluid medication dispenser of FIG. 3A and a second embodiment of a cover with stand.

FIGS. 7A-7C illustrate the third embodiment of the adaptable precision fluid medication dispenser system 300, further including a second embodiment of a cover 790. As shown in FIGS. 7A-7C, the cover 790 may contain the nozzle assembly 305, including nozzle 320 and arm 350, and may open in the direction of the nozzle 320 and arm 350.

Figure 8A:
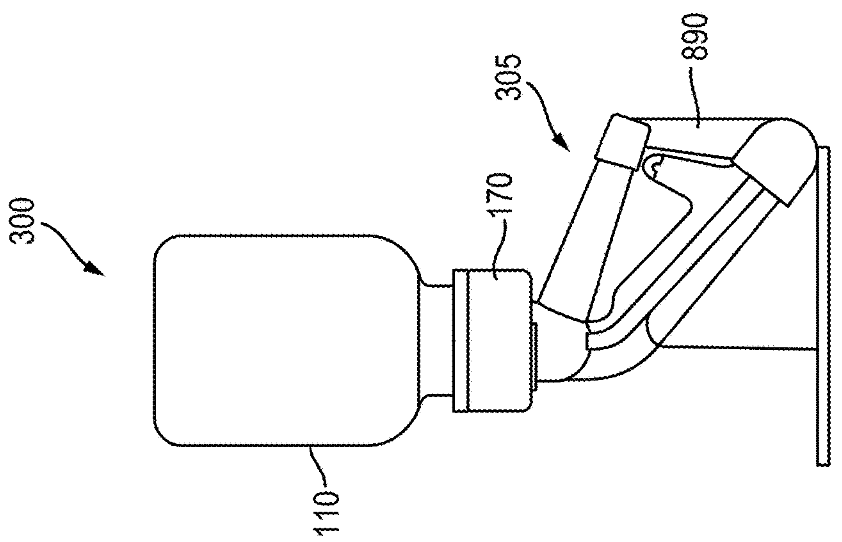
FIG. 8A is a side plan view of the adaptable precision fluid medication dispenser of FIG. 3A and a third embodiment of a cover with stand.
Figure 8B:
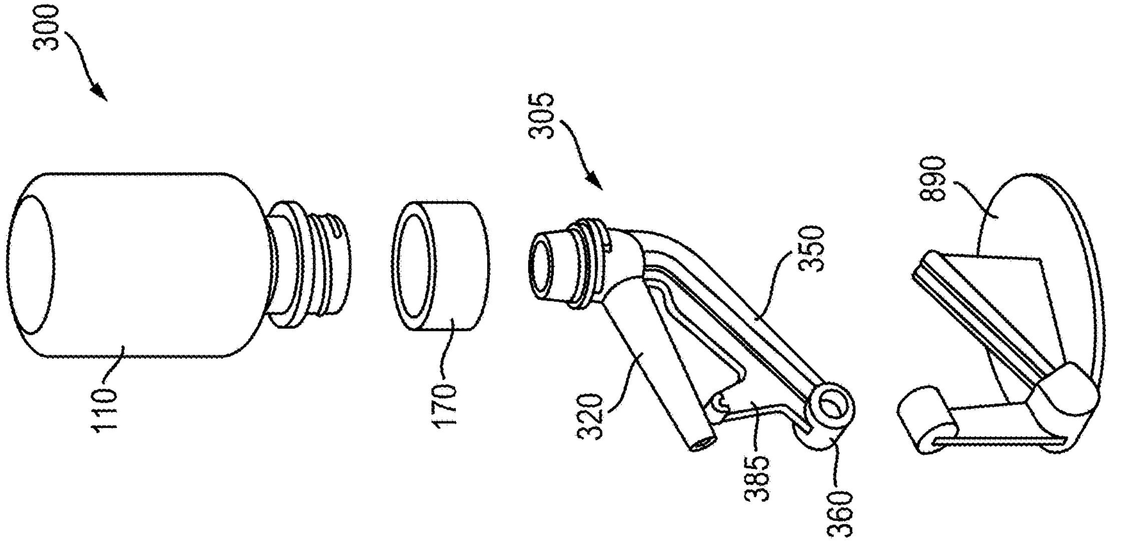
FIG. 8B is an exploded view of the adaptable precision fluid medication dispenser and cover with stand of FIG. 8A.
Figure 8C:
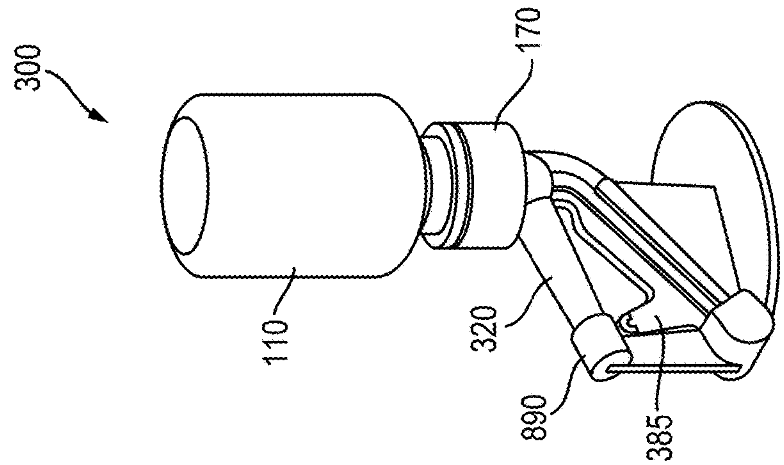
FIG. 8C is a front perspective view of the adaptable precision fluid medication dispenser and cover with stand of FIG. 8A.

FIGS. 8A-8C illustrate the third embodiment of the adaptable precision fluid medication dispenser system 300, further including a third embodiment of a cover 890. As shown in FIGS. 8A-8C, the cover 890 may contain only the distal end 335 of the nozzle 320, the skin engagement feature 360, and a portion of the arm 350, and can act as a display stand. The cover 890 can include a flat, wide base to support the nozzle assembly 305 and bottle 110 when the cover 890 acts as a display stand.

Figure 9C:
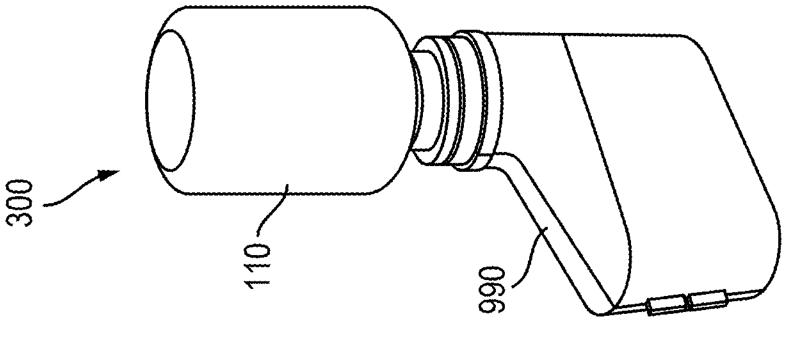
FIG. 9C is a top perspective view of the adaptable precision fluid medication dispenser and cover with stand of FIG. 9A in a closed position.
Figure 9B:
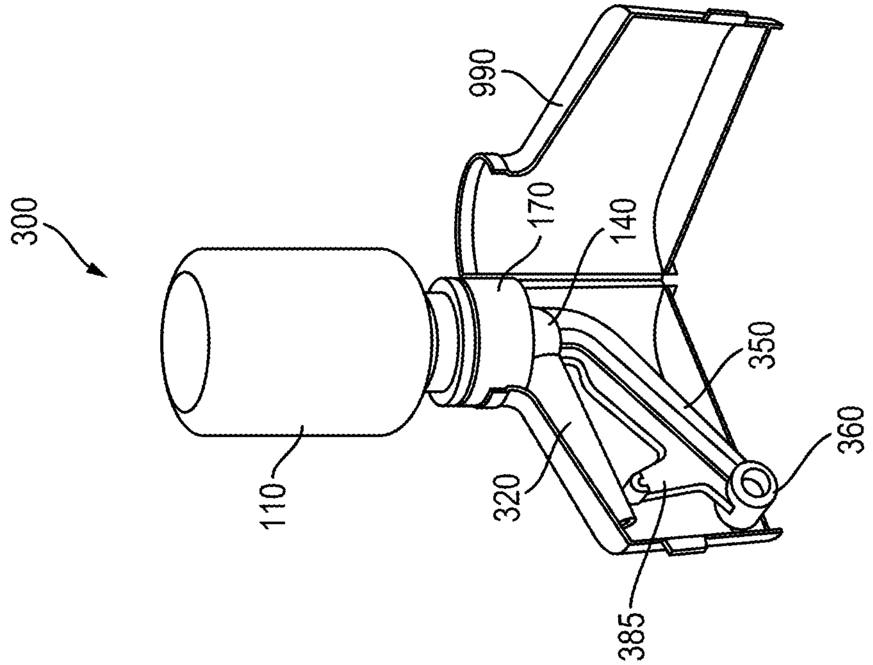
FIG. 9B is a top perspective view of the adaptable precision fluid medication dispenser and cover with stand of FIG. 9A in an open position.
Figure 9A:
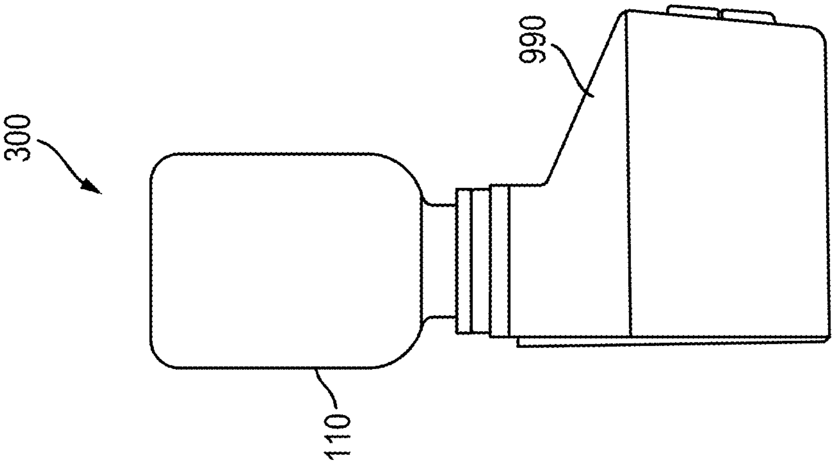
FIG. 9A is a side plan view of the adaptable precision fluid medication dispenser of FIG. 3A and a fourth embodiment of a cover with stand.

FIGS. 9A-9C illustrate the third embodiment of the adaptable precision fluid medication dispenser system 300, further including a fourth embodiment of a cover 990. As shown in FIGS. 9A-9C, the cover 990 may contain the nozzle assembly 305, including the nozzle 320 and arm 350, and may open in the direction perpendicular to the direction of the nozzle 320 and arm 350.

Figure 10B:
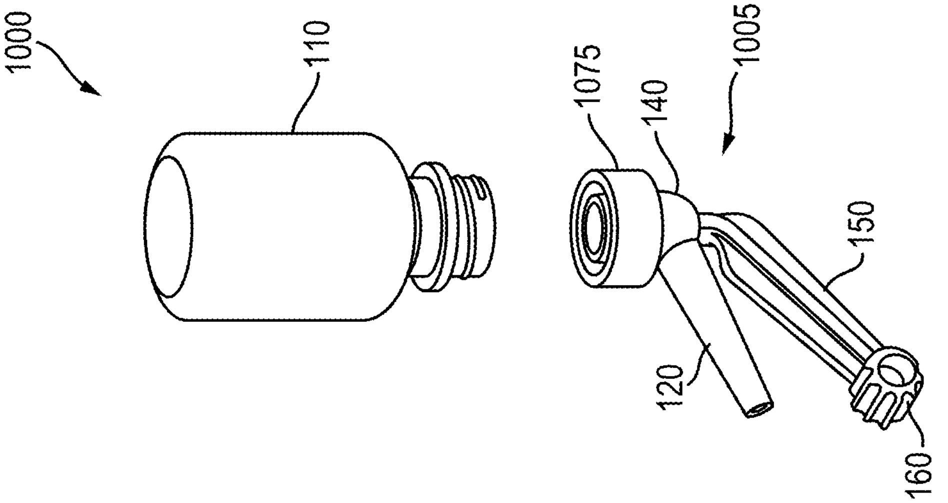
FIG. 10B is an exploded view of the adaptable precision fluid medication dispenser of FIG. 10A.
Figure 10A:
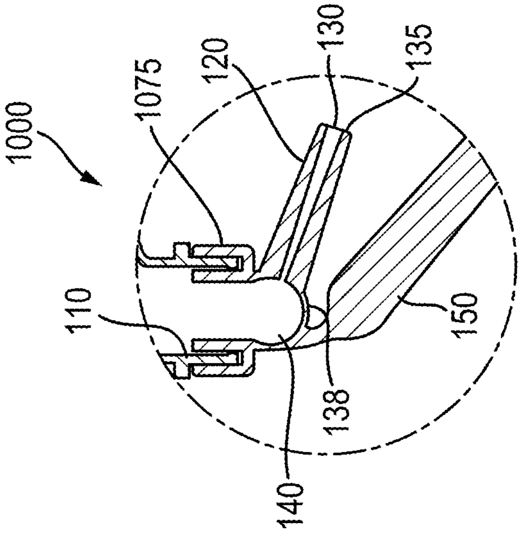
FIG. 10A is a cross sectional view of a nozzle of a seventh embodiment of an adaptable precision fluid medication dispenser.

FIGS. 10A-10B illustrate a seventh embodiment of the adaptable precision fluid medication dispenser system 1000, which includes features that are the same as or substantially similar to such features described above with respect to FIGS. 1A-1D, such that those features and their functions will not be repeated here for the sake of brevity. In some embodiments, such as that shown in FIGS. 10A-10B, the nozzle assembly 1005 can include a nozzle collar 1075, such that the nozzle assembly 1005 can be threaded onto a bottle 110 without the use of a separate collared cap, increasing convenience and ease of use. The nozzle collar 1075 can secure the nozzle assembly 1005 in place by threading around the standard bottle 110 threads. The nozzle collar 1075 can include a round cylindrical structure open on the bottom face, and inner threads configured to interface with a standard bottle 110. It is within the scope of this disclosure that any of the embodiments of the adaptable precision fluid medication dispenser system described herein can include a nozzle collar as part of the nozzle assembly or a separate collared cap.

Figure 11A:
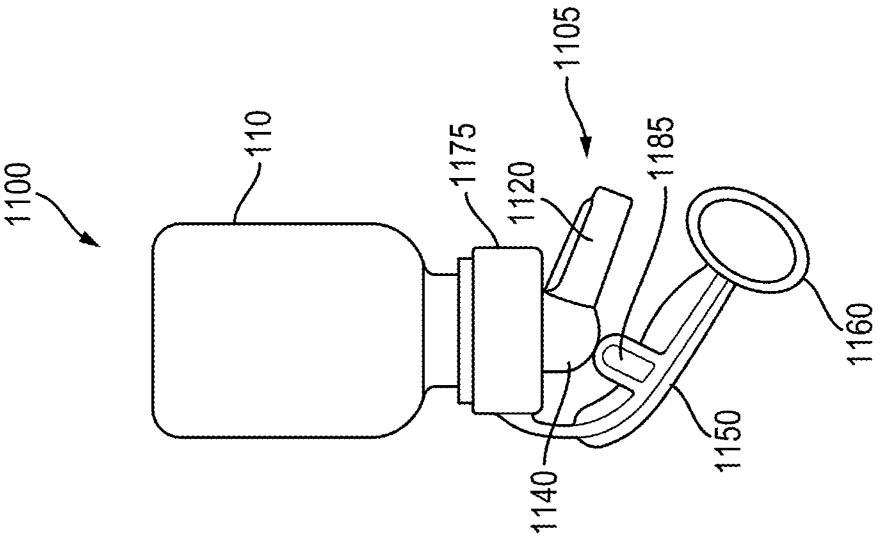
FIG. 11A is a side perspective view of an eighth embodiment of an adaptable precision fluid medication dispenser.
Figure 11B:
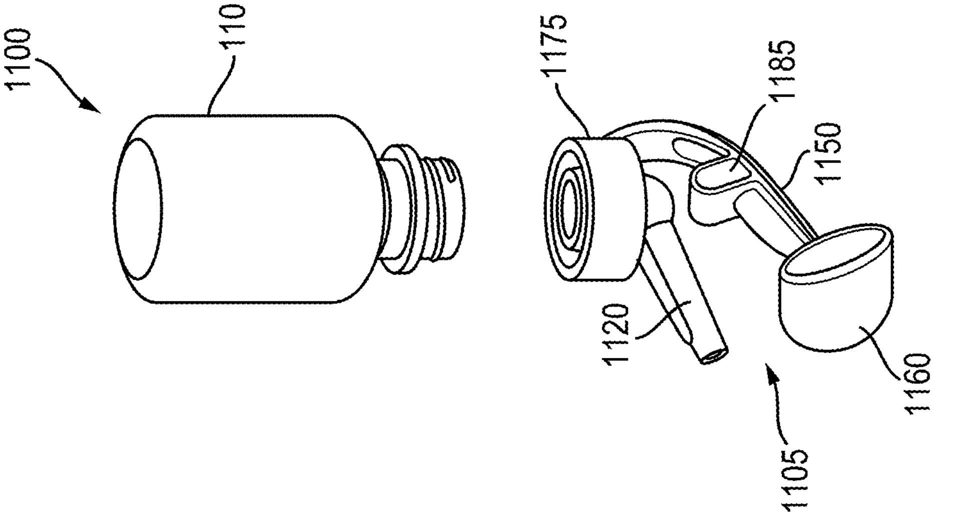
FIG. 11B is an exploded view of the adaptable precision fluid medication dispenser of FIG. 11A.
Figure 11C:
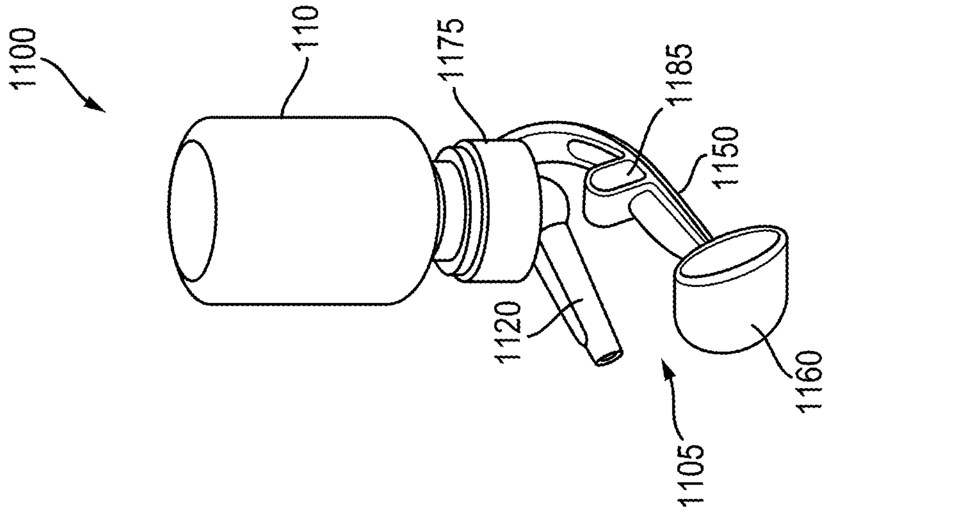
FIG. 11C is a top perspective view of the adaptable precision fluid medication dispenser of FIG. 11A.

FIGS. 11A-11C illustrate an eighth embodiment of the adaptable precision fluid medication dispenser system 1100 which includes features that are the same as or substantially similar to such features described above with respect to FIGS. 1A-1D, such that those features and their functions will not be repeated here for the sake of brevity. In some embodiments, such as that shown in FIGS. 11A-11C, nozzle assembly 1105 can include an arm 1150 extending from the nozzle collar 1175. The arm 1150 can include a protrusion 1185 configured to engage with and deform fluid chamber 1140. The nozzle 1120 and the fluid chamber 1140 may comprise a flexible or deformable material, such as a plastic, polymer, or the like. The nozzle collar 1175 and arm 1150 may comprise a comparatively stiff or less flexible material, such as a stiffer or less flexible plastic, polymer, or the like. The fluid chamber 1140 may be further configured such that deforming the fluid chamber 1140, such as by pressing from protrusion 1185, causes a dose volume of fluid to be dispensed from the hollow cylindrical portion of the nozzle 1120. The skin engagement feature 1160 can have a hollow cylindrical shape and can have a smooth surface to engage the lower eyelid area of the patient. The skin engagement feature 1160 can be tapered such that a length of a top side may be shorter than a length of a bottom side, as shown in FIG. 11C.

Figure 12A:
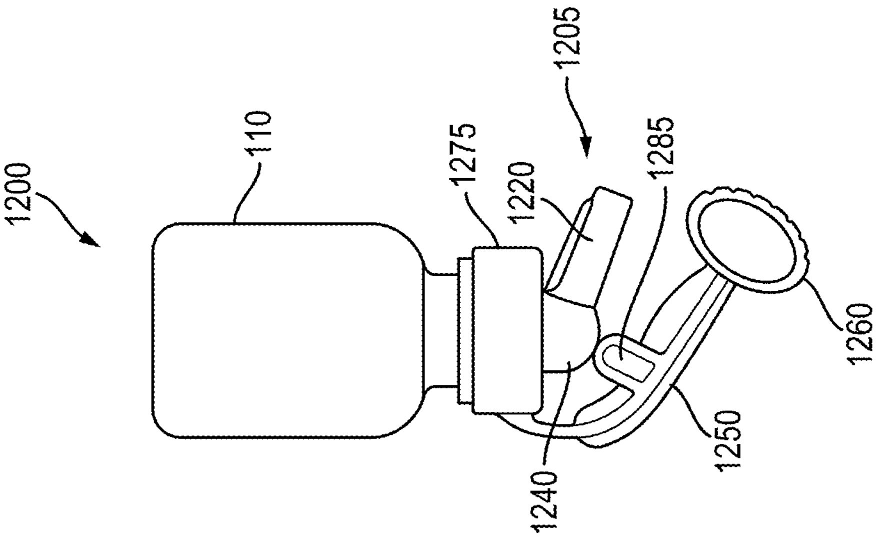
FIG. 12A is a side perspective view of a ninth embodiment of an adaptable precision fluid medication dispenser.
Figure 12B:
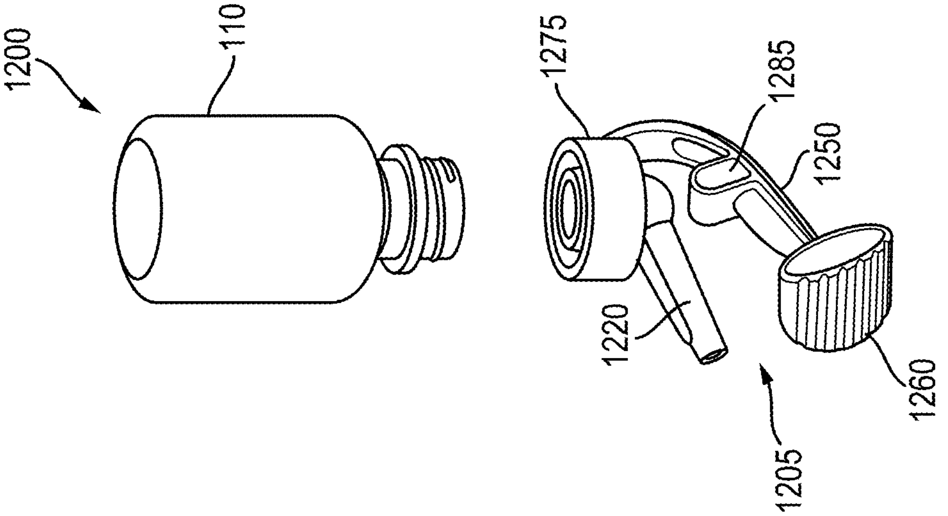
FIG. 12B is an exploded view of the adaptable precision fluid medication dispenser of FIG. 12A.
Figure 12C:
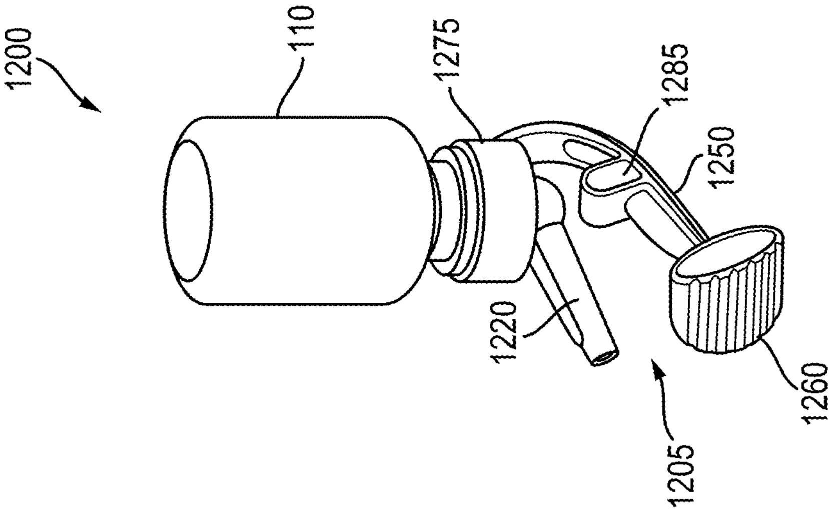
FIG. 12C is a top perspective view of the adaptable precision fluid medication dispenser of FIG. 12A.

FIGS. 12A-12C illustrate a ninth embodiment of the adaptable precision fluid medication dispenser system 1200 which includes features that are the same as or substantially similar to such features described above with respect to FIGS. 1A-1D, such that those features and their functions will not be repeated here for the sake of brevity. In some embodiments, such as that shown in FIGS. 12A-12C, nozzle assembly 1205 can include an arm 1250 extending from the nozzle collar 1275. The arm 1250 can include a protrusion 1285 configured to engage with and deform fluid chamber 1240. The nozzle 1220 and the fluid chamber 1240 may comprise a flexible or deformable material, such as a plastic, polymer, or the like. The nozzle collar 1275 and arm 1250 may comprise a comparatively stiff or less flexible material, such as a stiffer or less flexible plastic, polymer, or the like. The fluid chamber 1240 may be further configured such that deforming the fluid chamber 1240, such as by pressing from protrusion 1185, causes a dose volume of fluid to be dispensed from the hollow cylindrical portion of the nozzle 1220. The skin engagement feature 1260 can have a hollow cylindrical shape and can have a textured surface to engage the lower eyelid area of the patient. The textured surface can include one or more grooves and/or one or more protrusions. The skin engagement feature 1260 can be tapered such that a length of a top side may be shorter than a length of a bottom side, as shown in FIG. 12C.

Figure 13C:
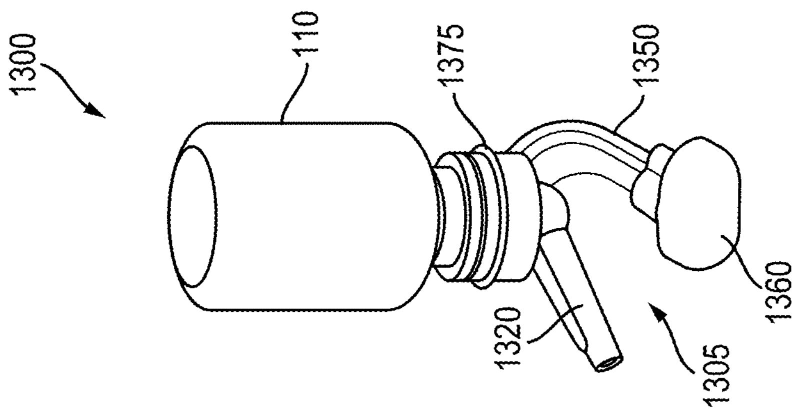
FIG. 13C is a top perspective view of the adaptable precision fluid medication dispenser of FIG. 13A.
Figure 13B:
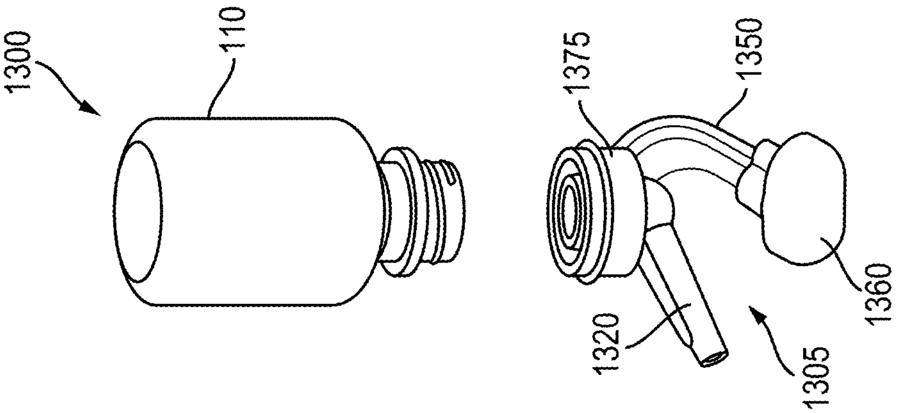
FIG. 13B is an exploded view of the adaptable precision fluid medication dispenser of FIG. 13A.
Figure 13A:
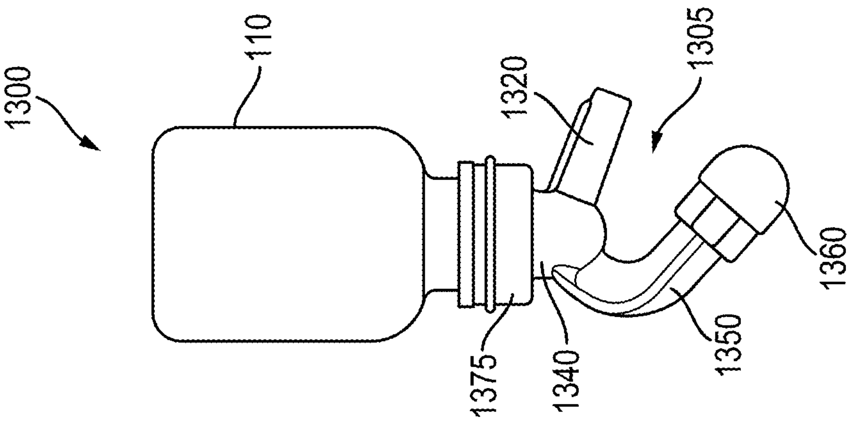
FIG. 13A is a side perspective view of a tenth embodiment of an adaptable precision fluid medication dispenser.

FIGS. 13A-13C illustrate a tenth embodiment of the adaptable precision fluid medication dispenser system 1300 which includes features that are the same as or substantially similar to such features described above with respect to FIGS. 1A-1D, such that those features and their functions will not be repeated here for the sake of brevity. In some embodiments, such as that shown in FIGS. 13A-13C, the nozzle assembly 1305 can include a nozzle 1320, a fluid chamber 1340, a nozzle collar 1375, and an arm 1350 extending from the fluid chamber 1340. A skin engagement feature 1360 may be located at the distal end of arm 1350, and the skin engagement feature 1360 can have a rounded ovular shape.

Figure 14A:
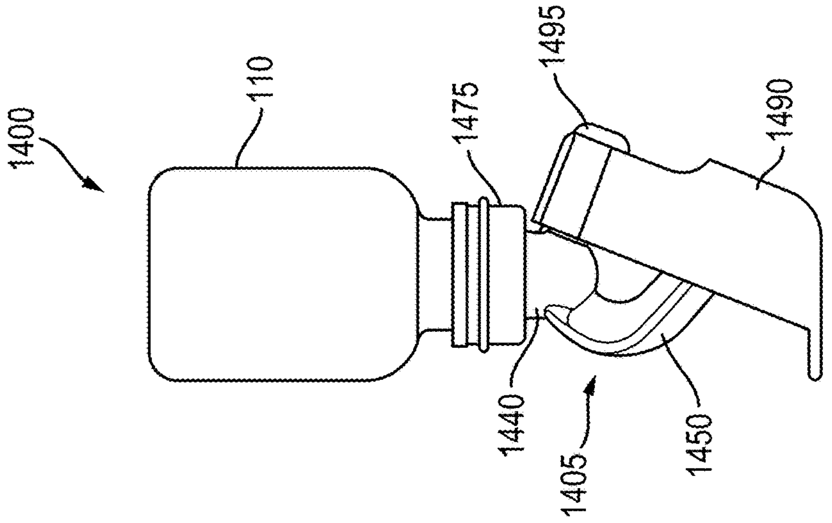
FIG. 14A is a side plan view of an eleventh embodiment of an adaptable precision fluid medication dispenser and a fourth embodiment of a cover.
Figure 14B:
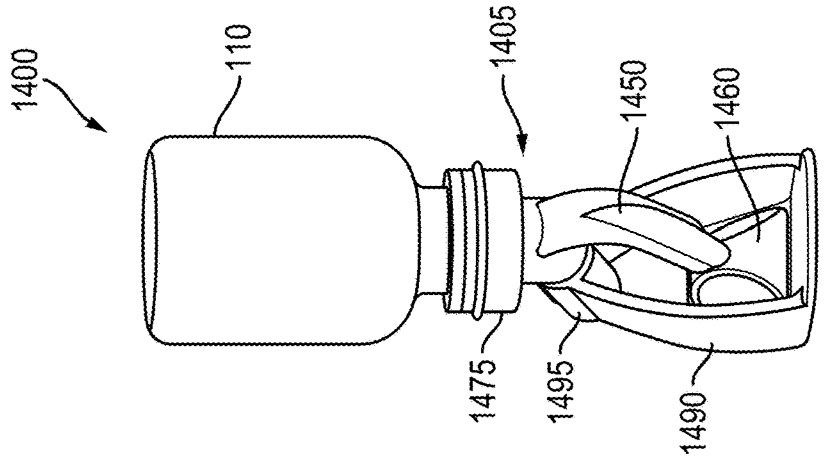
FIG. 14B is a side perspective view of the adaptable precision fluid medication dispenser and cover of FIG. 14A.
Figure 14C:
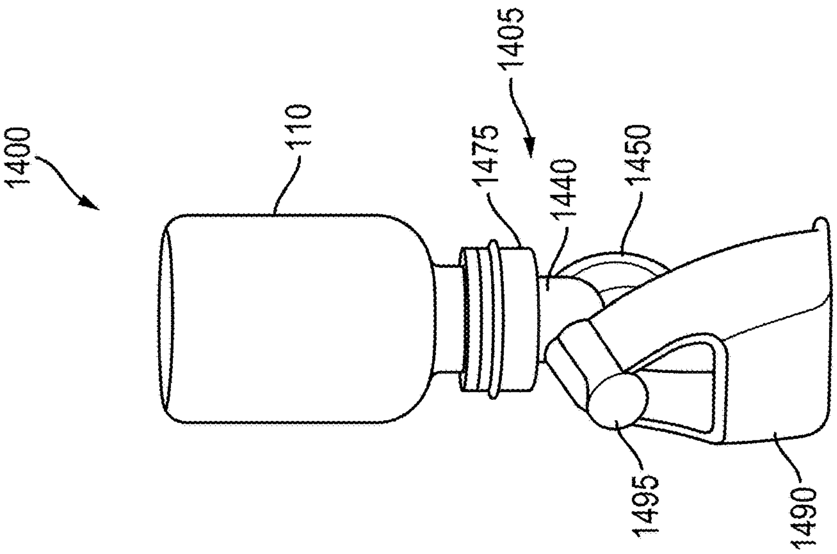
FIG. 14C is a side perspective view of the adaptable precision fluid medication dispenser and cover of FIG. 14A.

FIGS. 14A-14C illustrate an eleventh embodiment of the adaptable precision fluid medication dispenser system 1400, further including a fifth embodiment of a cover 1490, which includes features that are the same as or substantially similar to such features described above with respect to FIGS. 1A-1D, such that those features and their functions will not be repeated here for the sake of brevity. The nozzle assembly 1405 may include a nozzle collar 1475, an arm 1450, a fluid chamber 1440, a skin engagement feature 1460, and a nozzle 120. As shown in FIGS. 14A-C, the cover 1490 may surround and contain the nozzle 120 from the distal end 135 to the proximal end 138 with a nozzle cover portion 1495, and portions of cover 1490 may engage with the skin engagement feature 1460. The nozzle cover portion 1495 may occlude the distal end 135 of the nozzle 120, preventing liquid leaks through the nozzle 120. The cover 1490 may also include a flat portion so that the cover 1490 can act as a stand for the nozzle assembly 1405 and bottle 110.

FIGS. 15A-15G illustrate a twelfth embodiment of the adaptable precision fluid medication dispenser system 1500, which includes features that are the same as or substantially similar to such features described above with respect to FIGS. 1A-1D, such that those features and their functions will not be repeated here for the sake of brevity. As shown in FIGS. 15A-15G, the nozzle assembly 1505 can include a nozzle collar 1575, a nozzle 1520, a fluid chamber 1540, an arm 1550, and a skin engagement feature 1560. The nozzle 1520, nozzle collar 1575, fluid chamber 1540, arm 1550, and skin engagement feature 1560 may comprise a flexible or deformable material, such as a plastic, polymer, or the like. The nozzle 1520, nozzle collar 1575, fluid chamber 1540, arm 1550, and skin engagement feature 1560 may comprise the same material and may be formed integrally as a single object. The arm 1550 can include a groove 1580.

Figure 15A:
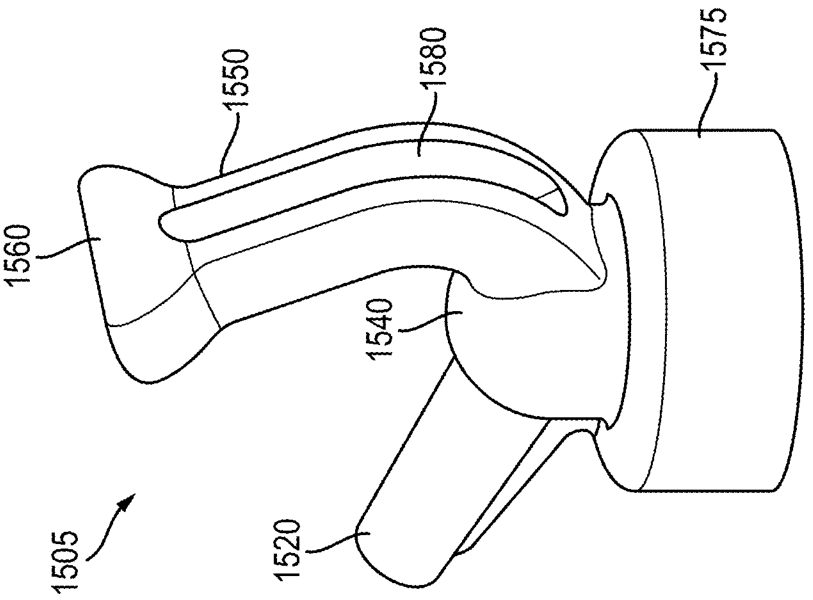
FIG. 15A is a side perspective view of a twelfth embodiment of an adaptable precision fluid medication dispenser.
Figure 15B:
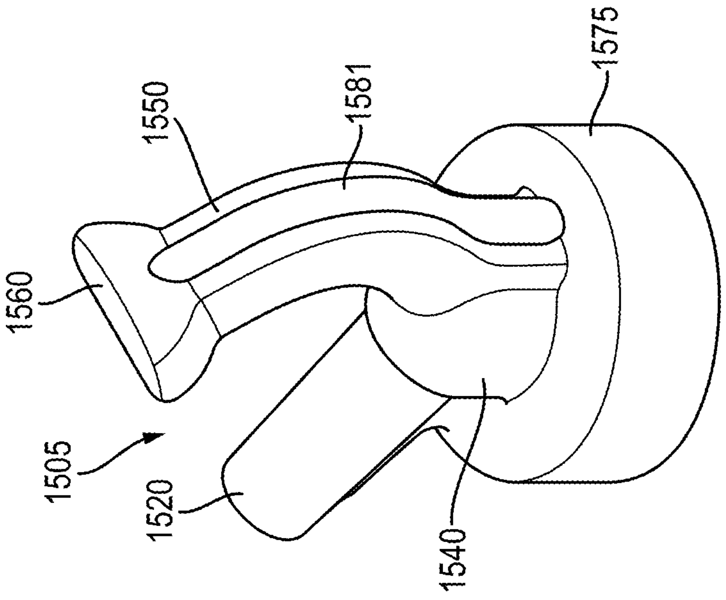
FIG. 15B is a side perspective view of a first embodiment of a backbone with the adaptable precision fluid medication dispenser of FIG. 15A.
Figure 15C:
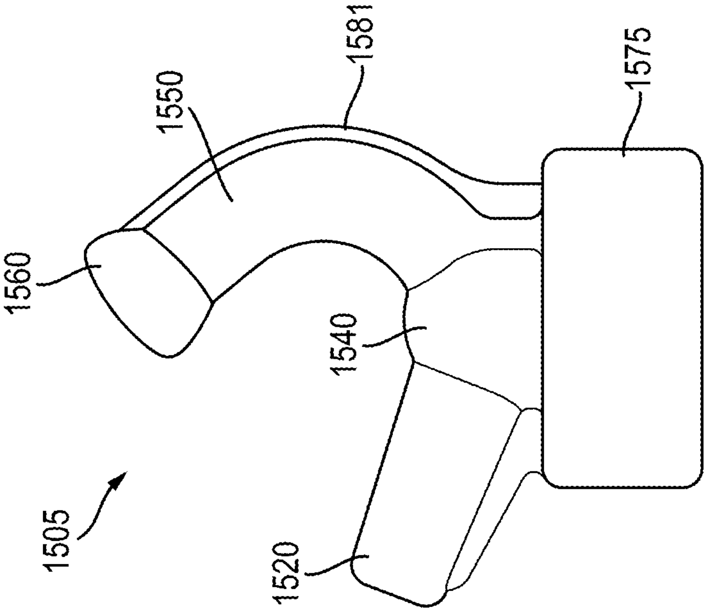
FIG. 15C is a side plan view of the backbone of FIG. 15B with the adaptable precision fluid medication dispenser of FIG. 15A.
Figure 15E:
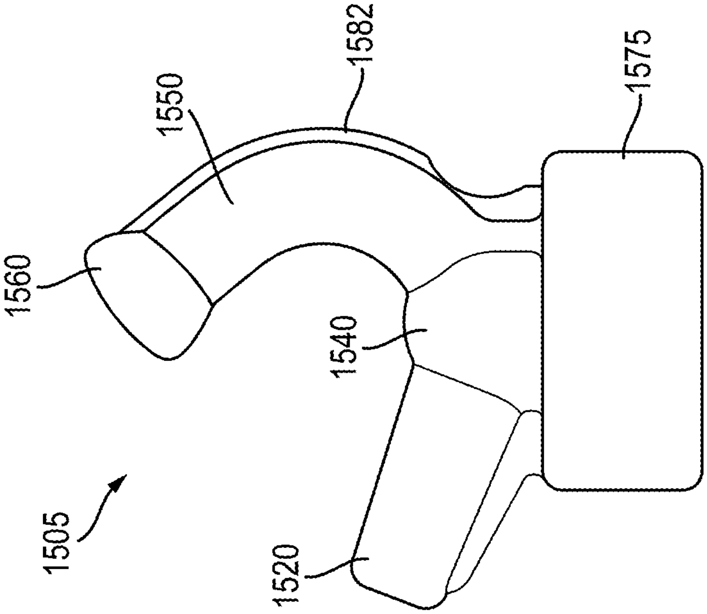
FIG. 15E is a side plan view of the backbone of FIG. 15D with the adaptable precision fluid medication dispenser of FIG. 15A.
Figure 15D:
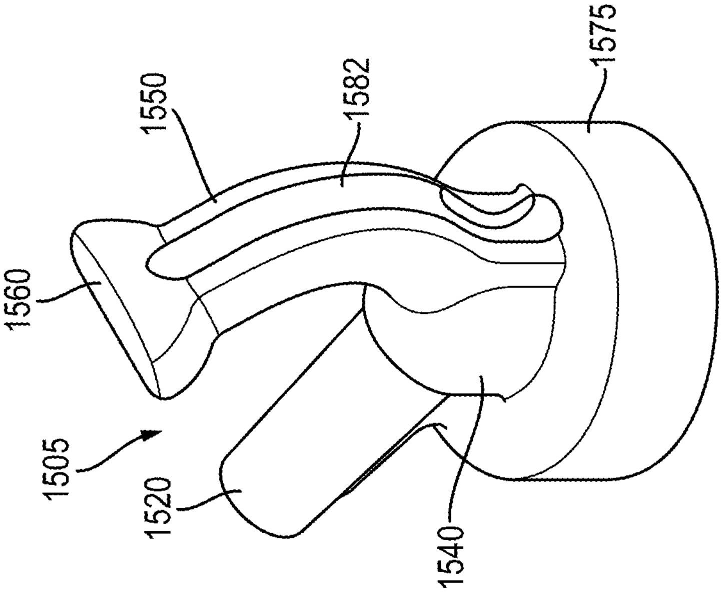
FIG. 15D is a side perspective view of a second embodiment of a backbone with the adaptable precision fluid medication dispenser of FIG. 15A.
Figure 15G:
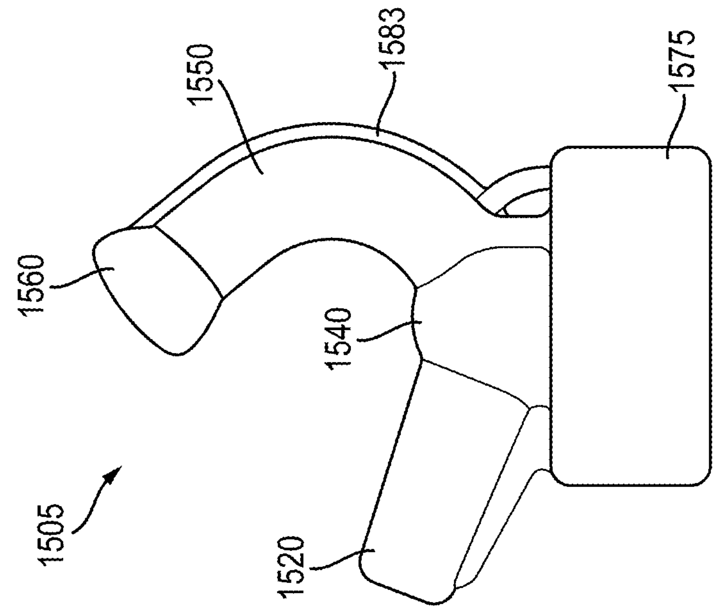
FIG. 15G is a side plan view of the backbone of FIG. 15F with the adaptable precision fluid medication dispenser of FIG. 15A.
Figure 15F:
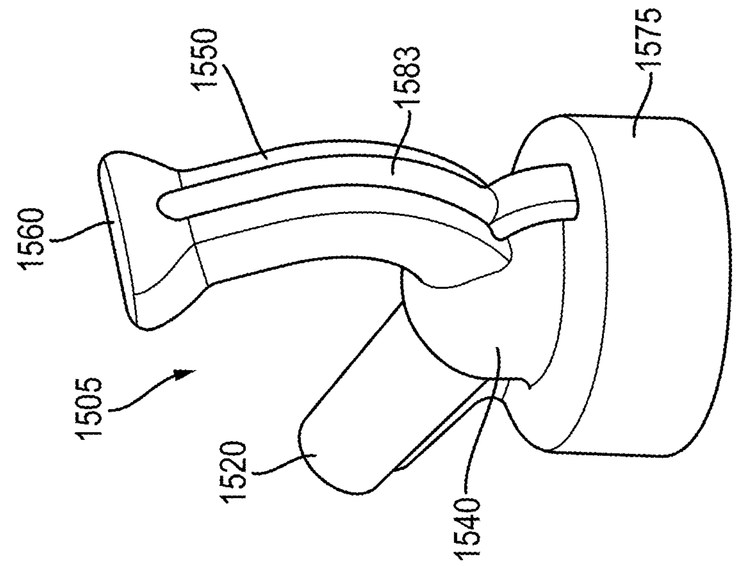
FIG. 15F is a side perspective view of a third embodiment of a backbone with the adaptable precision fluid medication dispenser of FIG. 15A.

As shown in FIGS. 15B-15G, a backbone 1581, 1582, 1583 may be located within the groove 1580. The backbone 1581, 1582, 1583 may comprise a comparatively stiff or less flexible material than one or more of the nozzle 1520, nozzle collar 1575, fluid chamber 1540, arm 1550, and skin engagement feature 1560, such as a stiffer or less flexible plastic, polymer, or the like. The backbone 1581, 1582, 1583 can have a variety of shapes, which can affect the overall flexibility and movability of the arm 1550. As shown in FIGS. 15B-15C, the backbone 1581 may extend from the distal end of arm 1550 to the top surface of the nozzle collar 1575, conforming to the contours of the arm 1550. As shown in FIGS. 15D-15E, the backbone 1582 may be substantially similar to the backbone shown in FIGS. 15B-15C, and further include a notch located at or adjacent to the proximal end of arm 1550. As shown in FIGS. 15F-15G, the backbone 1583 may conform to the contours of arm 1550 for only a portion of arm 1550, and can include a curved portion at or adjacent to the proximal end of arm 1550. The curved portion of the backbone 1583 can extend away from arm 1550 and engage with the upper surface of nozzle collar 1575.

It is within the scope of this disclosure that one or more of the various features described herein can be used with one or more of the various embodiments described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An adaptable precision fluid dispenser system for use with a container of a type configured for holding a fluid and defining an orifice for dispensing the fluid and a central longitudinal axis aligned with the orifice, the adaptable precision fluid dispenser system comprising:

a nozzle assembly comprising:

a fluid chamber configured for coupling to the orifice of the container for receiving the fluid exiting the orifice;

a nozzle fixed to the fluid chamber and having a nozzle end in fluid communication with the fluid chamber, to thereby permit dispensing of the fluid from the nozzle end into an eye of a user; and an arm extending at an angle relative to the nozzle and having a skin engaging tip configured for engaging skin surrounding the eye to assist with dispensing the fluid in the eye;

wherein the nozzle and the arm each extend relative to the fluid chamber in oblique relation to the longitudinal axis of the container when the fluid chamber is coupled to the orifice of the container; and wherein, when the skin engaging tip of the arm is in engaged relation with the skin surrounding the eye, manipulation of the container causes the arm to pivot or move relative to at least the container from an initial condition to a flexed condition to cause the skin engaging tip to move inwardly toward the nozzle to thereby retract the skin surrounding the eye and position the nozzle end of the nozzle in alignment with the eye for dispensing of the fluid.

2. The adaptable precision fluid dispenser system of claim 1, wherein the arm is configured to pivot relative to the nozzle.

3. The adaptable precision fluid dispenser system of claim 2, wherein the skin engaging tip is configured to engage a lower eyelid thereby allowing the arm to move the lower eyelid relative to the eye upon movement of the arm.

4. The adaptable precision fluid dispenser system of claim 3, wherein the arm is formed of a flexible material thereby allowing the arm to bend and the arm to pivot relative to the nozzle during manipulation of the container.

5. The adaptable precision fluid dispenser system of claim 2, wherein the skin engaging tip of the arm includes one or more of a hollow circular cylinder, a hollow ovular cylinder, and a rounded protrusion.

6. The adaptable precision fluid dispenser system of claim 2, wherein the skin engaging tip of the arm includes a smooth surface.

7. The adaptable precision fluid dispenser system of claim 2, wherein the skin engaging tip of the arm includes one of a surface texture, grooves or protrusions.

8. The adaptable precision fluid dispenser system of claim 2, wherein the skin engaging tip of the arm is configured to frictionally engage a lower eyelid of the eye of the user thereby causing the arm to move the lower eyelid relative to the eye.

9. The adaptable precision fluid dispenser system of claim 1, wherein the arm is configured to deform at least one of the nozzle or the fluid chamber to facilitate dispensing of the fluid from the nozzle end.

10. The adaptable precision fluid dispenser system of claim 9, wherein the arm comprises a protrusion configured to engage and deform the at least one of the nozzle or the fluid chamber.

11. The adaptable precision fluid dispenser system of claim 1, wherein the arm is configured to deform the container to facilitate dispensing of the fluid from the nozzle end.

12. The adaptable precision fluid dispenser system of claim 1 including a nozzle collar for releasably securing the nozzle assembly to the container, the nozzle collar including a thread configured to couple with a corresponding thread of the container.

13. The adaptable precision fluid dispenser system of claim 1, wherein the arm comprises a first material and the nozzle and the fluid chamber comprise a second material, wherein the first material and the second material are different and wherein the second material is more flexible than the first material.

14. The adaptable precision fluid dispenser system of claim 1, further comprising a cover configured to engage with at least one of the nozzle and the arm, the cover configured to occlude the nozzle end of the nozzle.

15. The adaptable precision fluid dispenser system of claim 1 wherein the nozzle is arranged about a nozzle axis and the arm is arranged about an arm axis and wherein each of the nozzle axis and the arm axis extend in oblique relation to a longitudinal axis defined by the container when the fluid chamber is coupled to the orifice of the container.

16. The adaptable precision fluid dispenser system of claim 15 wherein the nozzle axis of the nozzle is at a first angle relative to the longitudinal axis of the container ranging from 65 degrees to 75 degrees when the fluid chamber is coupled to the orifice of the container, and wherein the arm axis of the arm is at a second angle relative to the longitudinal axis of the container ranging from 40 degrees to about 60 degrees when the fluid chamber is coupled to the orifice of the container and when in the initial condition of the arm, wherein the first angle is greater than the second angle.

17. The adaptable precision fluid dispenser system of claim 1 wherein the arm includes a first end and a second end, the first end secured to the fluid chamber and the second end having the skin engaging tip.

18. The adaptable precision fluid dispenser system of claim 1 including the container for holding a fluid and defining the orifice for dispensing the fluid, the container being securable to the fluid chamber.

19. The adaptable precision fluid dispenser system of claim 1, wherein the arm includes a secondary arm segment having a container engagement feature opposite the skin engaging tip, the container engagement feature configured to engage with and deform the container during pivoting movement of the arm.

20. An adaptable precision fluid dispenser system comprising:

a nozzle assembly adaptable to a container, the nozzle assembly comprising:

a nozzle having a nozzle end and arranged about a nozzle axis;

a fluid chamber in fluid communication with the nozzle, the fluid chamber configured for accommodating a fluid and enabling passage of the fluid for dispensing from the nozzle end of the nozzle into an eye of a user; and an arm including a first end secured to the fluid chamber and a second end remote from the first end, the arm extending at an oblique angle relative to the nozzle and having a skin engaging tip at the second end configured for engaging skin surrounding the eye, the arm including one of a protruding segment or extension extending toward the nozzle;

wherein, when the skin engaging tip of the arm is in engaged relation with the skin surrounding the eye, manipulation of the container causes: 1) the arm to move relative to the nozzle or the fluid chamber to cause the skin engaging tip to move toward the nozzle and displace the skin surrounding the eye and 2) the one of a protruding segment or extension of the arm to deform the nozzle or the fluid chamber inwardly relative to the nozzle axis to cause dispensing of the fluid from the nozzle end of the nozzle and into the eye of the user.

21. The adaptable precision fluid dispenser system of claim 20, wherein the one of a protruding segment or extension of the arm is configured to engage and deform the fluid chamber during movement thereof relative to the nozzle or the fluid chamber.

22. The adaptable precision fluid dispenser system of claim 21, wherein the arm is configured to pivot relative to the nozzle or the fluid chamber.

23. The adaptable precision fluid dispenser system of claim 20 wherein the nozzle is arranged about a nozzle axis and the arm is arranged about an arm axis and wherein each of the nozzle axis and the arm axis extend in oblique relation to a longitudinal axis of the container when the fluid chamber is coupled to the container.

24. The adaptable precision fluid dispenser system of claim 23 wherein the nozzle axis of the nozzle is at a first angle relative to the longitudinal axis of the container ranging from 65 degrees to 75 degrees when the fluid chamber is coupled to the container, and wherein the arm axis of the arm is at a second angle relative to the longitudinal axis of the container ranging from 40 degrees to about 60 degrees when the fluid chamber is coupled to the container, wherein the first angle is greater than the second angle.

25. The adaptable precision fluid dispenser system of claim 20 including the container for holding a fluid and defining an orifice for dispensing the fluid, the container being securable to the fluid chamber.

26. A method, comprising:

coupling a nozzle assembly to a fluid container, the nozzle assembly including a nozzle having a nozzle end, a fluid chamber in communication with the nozzle end for passage of fluid and an arm depending at an angle relative to the nozzle, wherein the nozzle and the arm each extend relative to the fluid chamber in oblique relation to a longitudinal axis of the fluid container when the fluid chamber is coupled to an orifice of the fluid container;

positioning a skin engaging tip of the arm relative to skin surrounding an eye of a user;

manipulating the fluid container to cause the skin engaging tip of the arm to move toward the nozzle such that the skin engaging tip moves the skin surrounding the eye; and dispensing the fluid from the nozzle end of the nozzle and into the eye.

27. The method according to claim 26 wherein manipulating the fluid container includes:

causing the arm to engage and deform at least one of the nozzle or the fluid chamber to dispense the fluid from the nozzle end of the nozzle.

28. The method according to claim 26 wherein manipulating the fluid container causes the arm to pivot relative to the nozzle.

29. The method according to claim 28 wherein manipulating the fluid container is performed without engagement of the arm by the user.

30. The method according to claim 28 wherein the arm includes a secondary arm segment having a bottle engagement feature opposite the skin engaging tip, and wherein manipulating the fluid container includes:

causing the bottle engagement feature of the secondary arm segment to engage and deform the fluid container to dispense the fluid from the nozzle end of the nozzle.

* * * * *